US012729219B2

(12) United States Patent
Hu et al.

(10) Patent No.: US 12,729,219 B2
(45) Date of Patent: Sep. 8, 2026

(54) PROCESSES FOR PREPARING OLIGONUCLEOTIDES

(71) Applicants: CHANGZHOU SYNTHEALL PHARMACEUTICALS CO., LTD., Changzhou (CN); SHANGHAI STA PHARMACEUTICAL R&D CO., LTD., Shanghai (CN)

(72) Inventors: Chenchen Hu, Shanghai (CN); Qiang Zhao, Changzhou (CN); Qing Li, Changzhou (CN); Jimin Yang, Changzhou (CN)

(73) Assignees: CHANGZHOU SYNTHEALL PHARMACEUTICALS CO., LTD., Changzhou (CN); SHANGHAI STA PHARMACEUTICAL R&D CO., LTD., Shanghai (CN)

(*) Notice: Subject to any disclaimer, the term of this patent is extended or adjusted under 35 U.S.C. 154(b) by 690 days.

(21) Appl. No.: 18/066,867

(22) Filed: Dec. 15, 2022

(65) Prior Publication Data

US 2023/0212212 A1 Jul. 6, 2023

Related U.S. Application Data

(63) Continuation of application No. PCT/CN2020/101401, filed on Jul. 10, 2020.

(51) Int. Cl.
*C07H 19/16* (2006.01)
*C07H 1/00* (2006.01)

(52) U.S. Cl.
CPC ............... *C07H 19/16* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 8,969,551 B2 | 3/2015 | Ueda | |
| 10,415,036 B2 | 9/2019 | Torii et al. | |
| 2011/0059014 A1 | 3/2011 | Namavari et al. | |
| 2014/0315977 A1 | 10/2014 | Bestwick et al. | |
| 2018/0194795 A1* | 7/2018 | Hennecke | C40B 50/14 |

FOREIGN PATENT DOCUMENTS

| | | |
|---|---|---|
| CN | 101861318 | 10/2010 |
| CN | 102702265 | 10/2012 |
| CN | 103154009 | 6/2013 |
| CN | 105228999 | 1/2016 |
| CN | 105392884 | 3/2016 |
| EP | 2623507 | 8/2013 |
| JP | 2011503184 | 1/2011 |
| JP | 2016521119 | 7/2016 |
| WO | 01/02417 | 1/2001 |
| WO | 2009064471 | 5/2009 |
| WO | 2012043730 | 4/2012 |
| WO | 2014189142 | 11/2014 |

OTHER PUBLICATIONS

Noronha et al. Biochemistry (2000), vol. 39, pp. 7050-7062.*
International Search Report for PCT/CN2020/101401 dated Mar. 25, 2021, 3 pages.
Written Opinion of the ISA for PCT/CN2020/101401 dated Mar. 25, 2021, 5 pages.
Damaha et. al., "Chemical synthesis of branched RNA: novel trinucleoside diphosphates containing vicinal 2'-5' and 3", Tetrahedron Letters, (1985), vol. 26(40), ISSN 0005520312, pp. 4839-4842.
Ghodke wt al., "The N2-Furfuryl-deoxyguanosine Adduct Does Not Alter the Structure of B-DNA", J. Org. Chem., Dec. 9, 2015, vol. 81, ISSN 0005520313, pp. 502-511.
Gowda et al., "N2-Substituted 2\'-Deoxyguanosine Triphosphate Derivatives as Selective Substrates for Human DNA Polymerase k", Angew. Chem. Int. Ed, Jan. 31, 2017, vol. 56, pp. 2628-2631.

(Continued)

*Primary Examiner* — Patrick T Lewis
(74) *Attorney, Agent, or Firm* — NIXON & VANDERHYE, PC

(57) ABSTRACT

Disclosed are processes for preparing oligonucleotides. The process comprises: (a) converting a compound of Formula X-1 into a compound of Formula X-2: where $R^{10}$ is a residue of an oligonucleotide (e.g., a phosphorodiamidate morpholino oligomer); $R^{11}$ is an amine protecting group; wherein the compound of Formula X-1 is not bound to a solid support; and; (b) optionally removing protecting groups in the compound of Formula X-2 to obtain the olignucleotide. The synthetic processes described herein are advantageous in many aspects, including but not limited to improved yields and purities of target phosphorodiamidate morpholino oligomers with reduced 4-nitrostyrene adduct impurities. (X-1), (X-2)

X-1

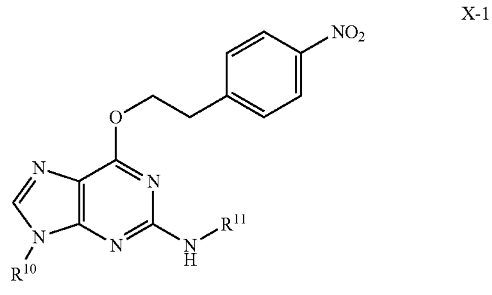

X-2

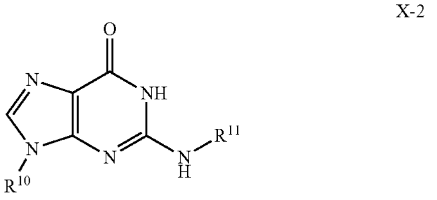

18 Claims, No Drawings

Specification includes a Sequence Listing.

(56) References Cited

OTHER PUBLICATIONS

Aubert et al., "Synthesis and anti-HIV-1 integrase activity of modified dinucleotides", European Journal of Medicinal Chemistry, Dec. 9, 2009, vol. 44, pp. 5029-5044.

Avino et al., "Use of NPE-Protecting Groups for the Preparation of Oligonucleotides Without Using Nucleophiles During the Final Deprotection", Nucleosides & Nucleotides, 1994, 13 (10), pp. 2059-2069.

* cited by examiner

PROCESSES FOR PREPARING OLIGONUCLEOTIDES

CROSS-REFERENCE TO RELATED APPLICATIONS

This application is a continuation of International Application No. PCT/CN2020/101401 filed Jul. 10, 2020 which designated the U.S., the entire contents of which are hereby incorporated by reference.

REFERENCE TO A SEQUENCE LISTING

This application contains a Sequence Listing, which is submitted electronically with a file name 6950-16_Sequence_Listing.xml, creation date of Dec. 15, 2022, and a size of 8 KB. This sequence listing submitted is part of the specification and is herein incorporated by reference in its entirety.

TECHNICAL FIELD

The present disclosure generally relates to processes for preparing oligonucleotides such as phosphorodiamidate morpholino oligomers (PMOs).

BACKGROUND

Phosphorodiamidate morpholino oligomers, or PMOs, are nucleic acid analogs which bind tightly and sequence specifically to complementary RNA and are useful in modulating protein synthesis and thus gene expression. These oligomers are composed of base-pairing recognition moieties (heterocyclic bases) supported by a morpholino backbone system. Morpholino subunits for use in synthesizing such oligomers can be prepared easily from the corresponding ribonucleosides, which are readily available and inexpensive precursors.

During such synthesis, as in conventional oligonucleotide synthesis, the functional groups on the heterocyclic bases are typically masked to prevent interference in the synthetic transformations.

It is known that the O6-unprotected guanine subunit gives rise to side reactions at the oligomer stage. For example, the O6 oxygen can react with activated subunit during coupling steps, to form O6-phosphorylated or derivative species, and during final cleavage of the base protecting groups with ammonia, ammonia can react at C6 to displace these species, giving a diaminopurine derivative. Such impurities are difficult to remove by chromatography, and cause a large loss in yield.

Various protection schemes have been proposed in the art to reduce side reactions of unprotected guanine O6-positions in conventional oligonucleotide synthesis. However, these protocols were largely unsuccessful when applied to phosphorodiamidate morpholino oligomers synthesis. Accordingly, improved methods are needed to increase yield and purity in phosphorodiamidate morpholino oligomers synthesis, particularly in the use of G morpholino subunits.

SUMMARY

Due to the specific challenges of the morpholino chemistry, a base protecting group should meet several requirements. The protecting group should be readily introduced onto the heterocyclic moiety and thereafter be stable to subunit activation and purification conditions, and solid phase synthesis. The protecting group should not be reactive with the morpholino amine moiety of the growing chain, and should allow the activated morpholino subunit to couple cleanly with the growing oligomer chain. The protecting group should be cleaved, preferably by ammonia, without introducing new impurities. Finally, it should result in crystalline subunit derivatives, in order to avoid the need for chromatographic purification prior to activation.

As described in US2009/0131624A1, the 4-nitrophenethyl (NPE) group at O6-positions does not adequately meet these criteria. The NPE group is cleaved with an alkaline reagent via a β-elimination mechanism. These conditions tend to generate the reactive by-product 4-nitrostyrene, which can then react with reactive sites on the oligomer. While various scavenging agents (e.g., thiols and 1,3-dicarbonyl compounds) were introduced into the deprotection mixture in an attempt to prevent trapping of the by-product by the oligomer, none were completely successful in eliminating this internal return problem. Even after purification, oligomers prepared with this subunit had a yellow tint. In various embodiments, the present disclosure provides methods and processes that are useful in solving one or more of these problems.

In one aspect, the present disclosure provides processes for preparing oligonucleotides such as phosphorodiamidate morpholino oligomers ("PMOs").

In further aspect, the present disclosure provides methods and compositions useful for preparing solid-phase-supported phosphorodiamidate morpholino oligonucleotides.

The synthetic processes for PMOs described herein are advantageous in many aspects, including but not limited to improved yields and purities of target phosphorodiamidate morpholino oligomers with reduced 4-nitrostyrene adduct impurities.

These and other objects and features of the disclosure will become more fully apparent when the following detailed description of the disclosure is read.

DETAILED DESCRIPTION OF THE DISCLOSURE

Exemplary Processes of Oligonucleotide Synthesis

The present disclosure provides a process for preparing an oligonucleotide, which comprises (a) converting a compound of Formula X-1 into a compound of Formula X-2:

X-1

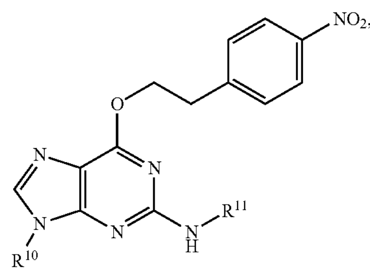

X-2

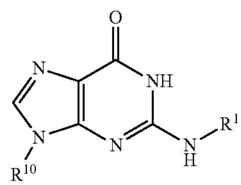

wherein:

$R^{10}$ is a residue of a starting oligonucleotide (e.g., a phosphorodiamidate morpholino oligomer);

$R^{11}$ is an amine protecting group;

preferably, the compound of Formula X-1 is not hound to a solid support; and (b) optionally removing protecting groups in the compound of Formula X-2 to obtain the oligonucleotide.

It should be clear to those skilled in the art that $R^{10}$ may be the same or different in Formula X-1 and X-2, depending on whether the residue of the starting oligonucleotide (e.g., a phosphorodiamidate morpholino oligomer) in Formula X-1 would change under the conditions where the NPE group is removed. For example, in some embodiments, other than the NPE group shown in Formula X-1, no other protecting groups are deprotected. $R^{10}$ can be the same in Formula X-1 and X-2. In some embodiments, $R^{10}$ in Formula X-2 can represent a deprotected version of $R^{10}$ in Formula X-1.

The oligonucleotide (and starting oligonucleotide) is not particularly limited. In some embodiments, the oligonucleotide is a phosphorodiamidate morpholino oligomer. Typically, the oligonucleotide comprises a targeting base sequence for sequence-specific binding to a target nucleic acid. Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary," Preferably, the oligonucleotide analog compounds employed in the presently described methods have at most one mismatch with the target sequence per every 10 nucleotides, and preferably at most one mismatch out of 20. Alternatively, the antisense oligomers employed have at least 80%, at least 90% sequence homology or at least 95% sequence homology, with the exemplary targeting sequences as designated herein. For purposes of complementary binding to an RNA target, and as discussed below, a guanine base may be complementary to either a cytosine or uracil RNA base.

Various amine protecting groups can be used as $R^{11}$. Typically, $R^{11}$ is an amine protecting group that can be removed by treatment with $NH_3$. For example, in some embodiments, $R^{11}$ is an acyl group, i.e., $R^B—C(=O)—$, wherein $R^B$ can be for example, hydrogen, alkyl, aryl, cycloalkyl, heteroaryl, each of which is optionally substituted. In some embodiments, $R^{11}$ is $—C(=O)—R^B$, wherein $R^B$ is an optionally substituted $C_{1-6}$ alkyl, e.g., a $C_{1-6}$ alkyl (e.g., isopropyl), an aryl substituted $C_{1-6}$ alkyl (e.g., benzyl), or an aryloxy substituted $C_{1-6}$ alkyl. In some specific embodiments, $R^{11}$ can be $—C(=O)—R^B$, wherein $R^B$ is a $C_{1-6}$ alkyl (e.g., isopropyl), an aryl (e.g., phenyl), or an awl substituted $C_{1-6}$ alkyl (e.g., benzyl), preferably, $R^B$ is isopropyl.

In some preferred embodiments, the compound of Formula X-1 is not bound to a solid support. Without wishing to be bound by theories, it is believed that without being bound to a solid support, the deprotection of the NPE group of Formula X-1 can be controlled such that the 4-nitrostyrene byproduct can preferentially react with a scavenger in the reaction medium over the compound of Formula X-2. However, in some embodiments, the compound of Formula X-1 can also be bound to a solid support and the reaction is controlled, for example, by adding excess amount of scavengers, such that the 4-nitrostyrene byproduct can preferentially react with a scavenger in the reaction medium over the compound of Formula X-2.

Conditions for converting the compound of Formula X-2 into the compound of Formula X-2 are not particularly limited. However, in some preferred embodiments, the converting comprises adding the compound of Formula X-1, preferably in a solution, into a mixture comprising an alkaline reagent (e.g., described herein) and a scavenger capable of reacting with the compound of Formula X-3:

X-3

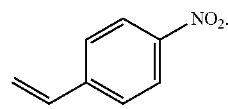

The alkaline reagent is typically a basic organic amine. For example, in some embodiments, the alkaline reagent is a basic organic amine having a pKa in water of about 9 or higher, such as about 9-15, about 10-14, about 12, about 13, or about 14. In some embodiments, the alkaline reagent is a basic cyclic, amine. In some embodiments, the alkaline reagent is 1,8-diazabicyclo[5.4.0]undec-7-ene ("DBU") or 1,5-diazabicyclo[4.3.0]non-5-ene ("DBN"). The alkaline reagent is typically added in excess, for example, the molar ratio of the alkaline reagent to the NPE group(s) of the compound of Formula X-1 is typically more than 1:1, such as 1.2:1, 1.5:1, 2:1, 5:1 or 10:1, or any range between the recited values, such as 1:1 to 10:1.

The scavenger is not particularly limited, so long as it can react with the byproduct of Formula X-3. Typically, the scavenger has a —SH or a 1,3-dicarbonyl moiety. In some embodiments, the scavenger can be a compound of Formula X-4:

X-4

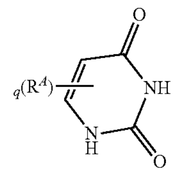

wherein:

q is 0, 1, or 2, and $R^A$ at each occurrence is independently an optionally substituted Cr alkyl (e.g., methyl).

In some embodiments, q is 0. In some embodiments, q is 1, and $R^A$ is an optionally substituted $C_{1-6}$ alkyl, such as methyl. $R^A$ can be attached to any of the available positions, provided that the compound of Formula X-4 can act as a scavenger of the compound of Formula X-3. In some specific embodiments, the scavenger is thymine or a derivative thereof in some specific embodiments, the scavenger is thymine.

The scavenger is typically also used in excess. For example, the molar ratio of the scavenger to the NPE group(s) of the compound of Formula X-1 is typically more than 1:1, such as 1.2:1, 1.5:1, 2:1, 5:1, 10:1, or any range between the recited values, such as 1:1 to 10:1. In cases where the compound of Formula X-1 has one or more bases that can react with 4-nitrostyrene; the amount of scavenger can be further increased, for example, up to 50:1 (or more) of the NPE group(s) of the compound of Formula X-1.

The conversion of Formula X-1 into Formula X-2 typically involves using one or more solvents. Various solvents are suitable. Non-limiting useful solvents include any of those described herein. For example, in some embodiments, the solvent can be an aprotic polar solvent, such as DMF, DMA, DMI, NMP and the like. In some preferred embodiments, the solvent can be NMP.

In some embodiments, the addition of the compound of Formula X-1 into the mixture of the alkaline reagent and the scavenger can be controlled such that the amount of NPE adduct to the oligonucleotide is minimized, for example, to be less than 10%, such as less than 5%.

In some embodiments, the process further comprises treating the compound of Formula X-2 with $NH_3$ to partially or fully remove the protecting groups in Formula X-2. For example, in some embodiments, is a $C_{1-6}$ alkyl-C(=O)—, upon treatment with $NH_3$, the $R^{11}$ group is removed to provide the deprotected base G.

An exemplified procedure of converting a compound of Formula X-1 into Formula X-2 is described herein, from which those skilled in the art can readily adapt to embodiments of the present disclosure.

Exemplary Processes of PMO Synthesis

In some specific embodiments, the present disclosure provides a process for preparing a PMO. In some embodiments, the process comprises:

(a) converting a compound of Formula X-5 into a compound of Formula X-6:

wherein.

m1 and m2 are independently an integer of 0-50 (e.g., 0-30);

$R^{11}$ is an amine protecting group;

Base at each occurrence is independently a base selected front G (guanine), C (cytosine), A (adenine), U (uracil), and T (thymine), modified analogs thereof, and protected derivatives thereof, provided that when the Base in Formula X-5 is a protected base, the corresponding Base in Formula X-6 can be the same protected base or a corresponding partially or fully deprotected base, wherein:

$T^1$ is a suitable 5' terminal group (e.g., a short peptide, optionally substituted alkylamino group, optionally substituted heterocyclic group, etc.); and $T^2$ is a suitable 3' terminal group, e.g., hydrogen or a protecting group (e.g., an acyl group, trityl, etc.); and (b) optionally partially or fully removing protecting groups in the compound of Formula X-6 to obtain the oligonucleotide.

The oligonucleotide of Formula X-5 or X-6 can have various number of G monomers at various positions of the sequence. In some embodiments, m1 is 0. In some embodiments, m2 is 0. In some embodiments, neither of m1 and m2 is 0. In some embodiments, the sum of m1 and m2 is

X-5

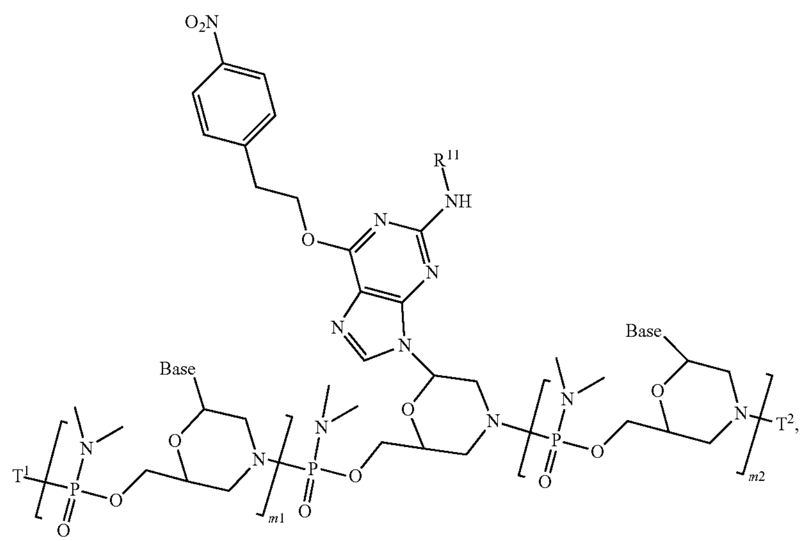

X-6

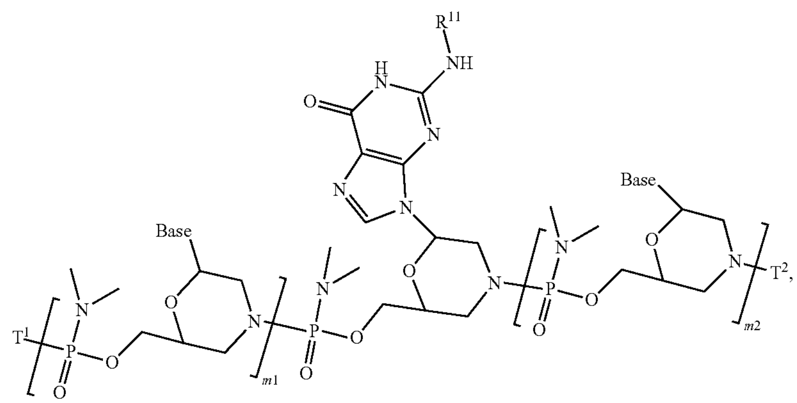

between 5 and 50, such as 5, 10, 15, 20, 25, 30, 35, 40, 45, 50, or any ranges between the recited values such as 10-40, 15-30, etc.

The Base in Formula X-5 or X-6 can be independently selected from G (guanine), C (cytosine), A (adenine), U (uracil), and T (thymine), modified analogs thereof, and protected derivatives thereof. Modified analogs as used herein include those non-standard bases such as 5-methyl cytosine, inosine (I) and 7-deaza-G bases. In some embodiments, the Base in Formula X-5 or X-6 can be independently selected from

PC

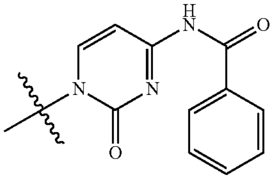

T

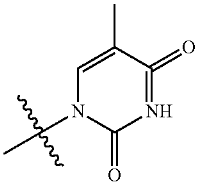

PA

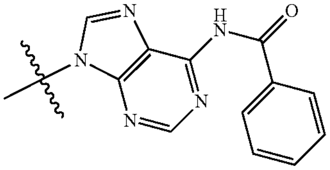

P5mC

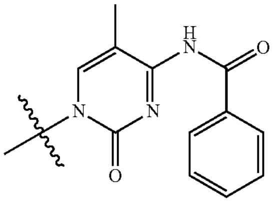

DPG

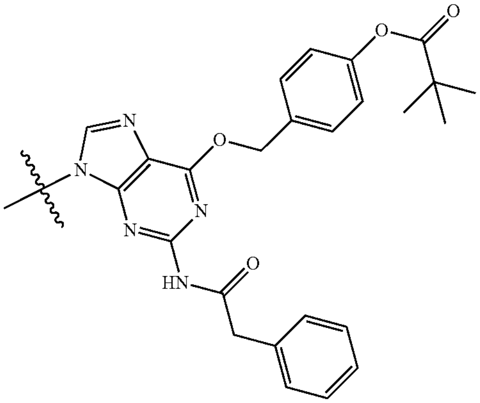

U

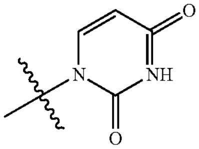

-continued

I

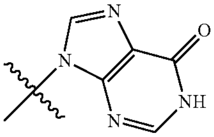

PG

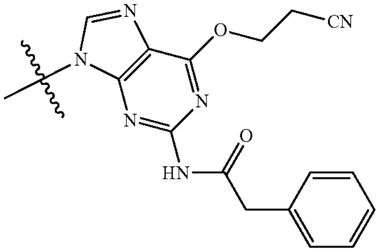

NPEG

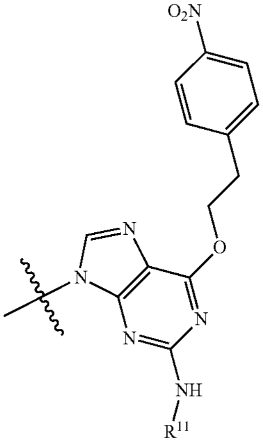

In some embodiments, when the Base in Formula X-5 is a G monomer unit, it can be NPEG,

NPEG

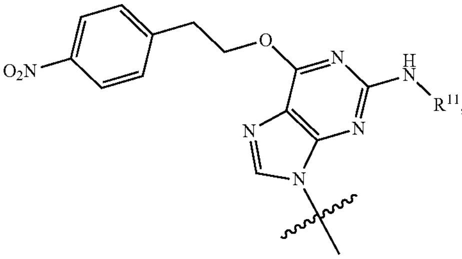

wherein $R^{11}$ is defined herein. In some embodiments, all of the G monomer units in Formula X-5 can be NPEG.

Oligonucleotides such as PMOs can have various terminus at the 5' or 3' end. For the synthetic processes described herein, the precise identity of such terminus is not critical and can include any of those known terminus suitable for PMOs.

In some embodiments, $T^1$ in Formula X-5 or X-6 can be an optionally substituted alkyl amine. e.g., —N($C_{1-6}$ alkyl)($C_{1-6}$ alkyl), wherein the two $C_{1-6}$ alkyl can be the same or different, and each of which can be optionally substituted, e.g., with an amide. In some embodiments, $T^1$ in Formula X-5 or X-6 can be an amide (e.g., —C(O)$NH_2$) substituted alkyl amine, e.g.,

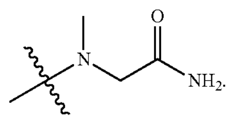 [SMILES: *N(C)CC(N)=O]

In some embodiments, $T^1$ in Formula X-5 or X-6 can be an optionally substituted heterocyclic ring, e.g., an optionally substituted 4-7 membered heterocyclic ring having 1 or 2 ring heteroatoms independently selected from N, O, and S, such as an optionally substituted piperizine ring, for example

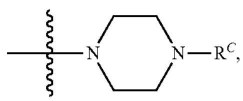

wherein $R^C$ is an acyl, acyloxy group, or a peptide residue.

In some embodiments, $T^2$ in Formula X-5 or X-6 can be hydrogen.

In some embodiments, $T^2$ in Formula X-5 or X-6 can be trityl or a methoxy substituted trityl group (e.g., MMT, DMT, etc.).

In some embodiments, $T^2$ in Formula X-5 or X-6 can be an acyl group (e.g., acetyl).

The PMO of Formula X-5 Or X-6 can have any sequence, which preferably comprises a targeting base sequence for sequence-specific binding to a target nucleic acid.

Various amine protecting groups can be used as $R^{11}$ in Formula X-5 or X-6. Typically, $R^{11}$ is an amine protecting group that can be removed by treatment with $NH_3$. For example, in some embodiments, $R^{11}$ is an acyl group, i.e., $R^B$—C(═O)—, wherein $R^B$ can be for example, hydrogen, alkyl, aryl, cycloalkyl, heteroaryl, each of which is optionally substituted. In some embodiments, $R^{11}$ is —C(═O)—$R^B$, wherein $R^B$ is an optionally substituted $C_{1-6}$ alkyl, e.g., a $C_{1-6}$ alkyl (e.g., isopropyl), an aryl substituted $C_{1-6}$ alkyl (e.g., benzyl), or an aryloxy substituted $C_{1-6}$ alkyl. In some specific embodiments, $R^{11}$ can be —C(═O)—$R^B$, wherein $R^B$ is a $C_{1-6}$ alkyl (e.g., isopropyl), an aryl (e.g., phenyl), or an aryl substituted $C_{1-6}$ alkyl (e.g., benzyl), preferably, $R^B$ is isopropyl.

In some preferred embodiments, the compound of Formula X-5 is not bound to a solid support.

Conditions for converting the compound of Formula X-5 into the compound of Formula X-6 are not particularly limited. However, in some preferred embodiments, the converting comprises adding the compound of Formula X-5, preferably in a solution, into a mixture comprising an alkaline reagent (e.g., described herein) and a scavenger capable of reacting with the compound of Formula X-3:

X-3

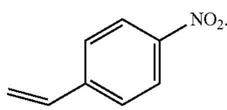

The alkaline reagent is typically a basic organic amine. For example, in some embodiments, the alkaline reagent is a basic organic amine having a pKa in water of about 9 or higher, such as about 9-15, about 10-14, about 12, about 13, or about 14. In some embodiments, the alkaline reagent is a basic cyclic amine. In some embodiments, the alkaline reagent is 1,8-diazabicyclo[5.4.0]undec-7-ene ("DBU") or 1,5-diazabicyclo[4.3.0]non-5-ene ("DBN"). The alkaline reagent is typically added in excess, for example, the molar ratio of the alkaline reagent to the NPE, group(s) of the compound of Formula X-5 is typically more than 1:1, such as 1.2:1, 1.5:1, 2:1, 5:1, 10:1, or any range between the recited values, such as 1:1 to 10:1.

The scavenger is not particularly limited, so long as it can react with the byproduct of Formula X-3, Typically, the scavenger has a —SH or a 1,3-dicarbonyl moiety. In some embodiments, the scavenger can be a compound of Formula X-4:

X-4

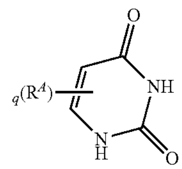

wherein:

q is 0, 1, or 2, and $R^A$ at each occurrence is independently an optionally substituted $C_{1-6}$ alkyl (e.g., methyl).

In some embodiments, q is 0. In some embodiments, q is 1, and $R^A$ is an optionally substituted $C_{1-6}$ alkyl, such as methyl. $R^A$ can be attached to any of the available positions, provided that the compound of Formula X-4 can act as a scavenger of the compound of Formula X-3. In some specific embodiments, the scavenger is thymine or a derivative thereof. In some specific embodiments, the scavenger is thymine.

The scavenger is typically also used in excess. For example, the molar ratio of the scavenger to the NPE group(s) of the compound of Formula X-5 is typically more than 1:1, such as 1.2:1, 1.5:1, 2:1, 5:1, 10:1, or any range between the recited values, such as 1:1 to 10:1. In cases where the compound of Formula X-5 has one or more bases that can react with 4-nitrostyrene, the amount of scavenger can be further increased, for example, up to 50:1 (or more) of the NPE group(s) of the compound of Formula X-5.

The conversion of Formula X-5 into Formula X-6 typically involves using one or more solvents. Various solvents are suitable. Non-limiting useful solvents include any of those described herein. For example, in some embodiments, the solvent can be an aprotic polar solvent, such as DMF, DMA, DMI, NMP and the alike. In some preferred embodiments, the solvent can be NMP.

In some embodiments, the addition of the compound of Formula X-5 into the mixture of the alkaline reagent and the scavenger can be controlled such that the amount of NPE adduct to the oligonucleotide is minimized, for example, to be less than 10%, such as less than 5%, In some embodiments, the process further comprises treating the compound of Formula X 6 with $NH_3$ to partially or fully remove the protecting groups in Formula X-6. For example, in some embodiments, $R^{11}$ is a $C_{1-6}$ alkyl-C(═O)—, upon treatment with $NH_3$, the $R^{11}$ group is removed to provide the deprotected base G.

The compound of Formula X-5 can be readily prepared by those skilled in the art in view of the present disclosure. For example, in some embodiments, the compound of Formula X-5 can be prepared by a process comprising cleaving a solid support from an oligonucleotide of Formula X-7, for example, with $NH_3$:

X-7

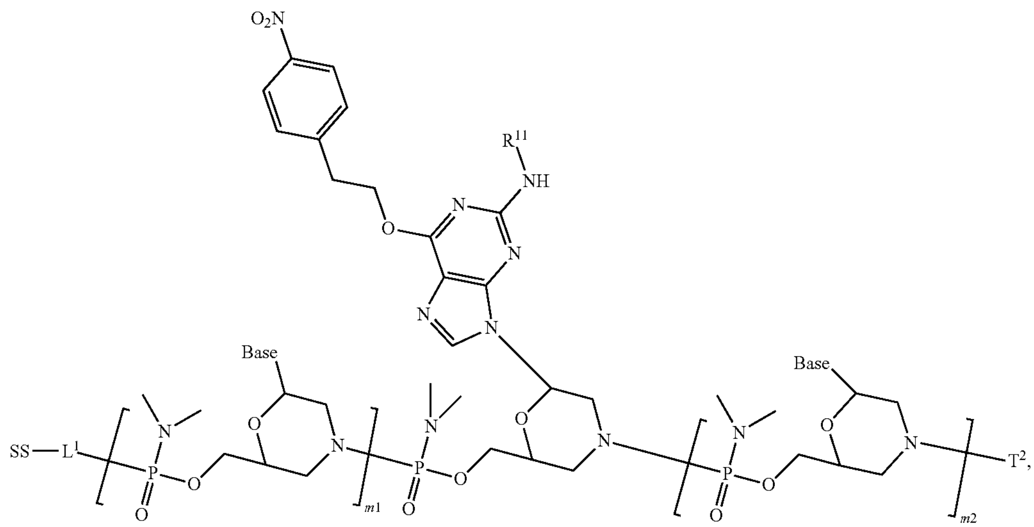

wherein

SS is a solid phase support, such as a polystyrene solid support, $L^1$ is a linker, such as a sarcosine based linker, e.g.,

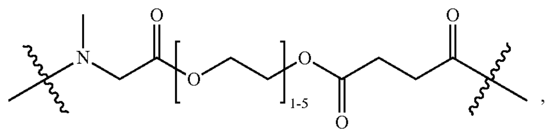

wherein the nitrogen end is linked to the phosphorous atom and the carbonyl end forms an amide linkage with the solid support;

m1, m2, and $R^{11}$ in Formula X-7 are the same as the corresponding groups in Formula X-5, Base at each occurrence is independently a base selected from G (guanine), C (cytosine), A (adenine), U (uracil), and T (thymine), analogs thereof and protected derivatives thereof, provided that when the Base in Formula. X-7 is a protected base, the corresponding base in Formula X-5 can be the same protected base or a corresponding partially or fully deprotected base; and $T^2$ is a suitable 3' terminal group, e.g., hydrogen or a protecting group (e.g., an acyl group, trityl).

In some embodiments, SS is a solid support such as a polystyrene solid support, having—$CH_2$—$NH_2$ groups, alternatively referred as SS—$CH_2$—$NH_2$.

In some embodiments, $L^1$ is a sarcosine based linker, e.g.,

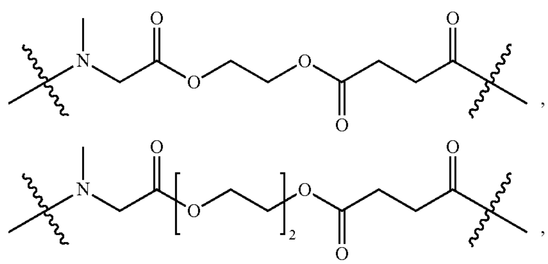

-continued

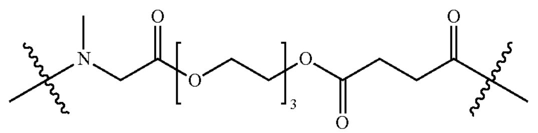

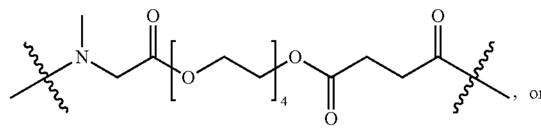

or

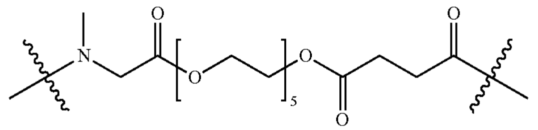

wherein the nitrogen end is linked to the phosphorous atom and the carbonyl end forms an amide linkage with the solid support.

In some embodiments, the Base in Formula X-7 can be independently selected from

PC

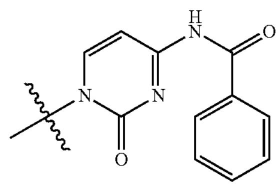

T

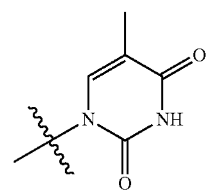

-continued

PA

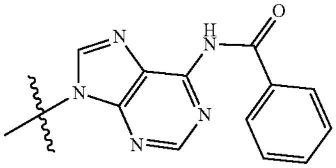

P5mC

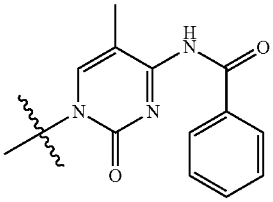

DPG

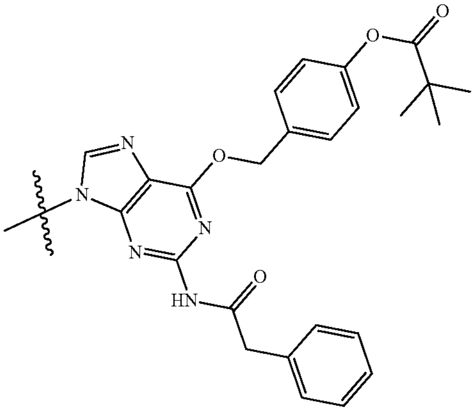

U

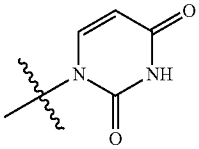

I

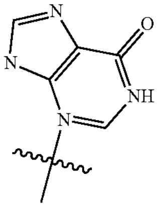

PG

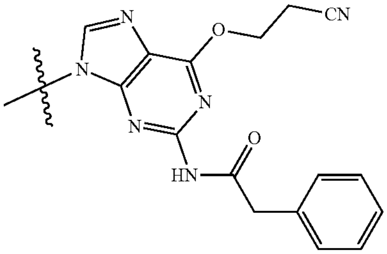

-continued

NPEG

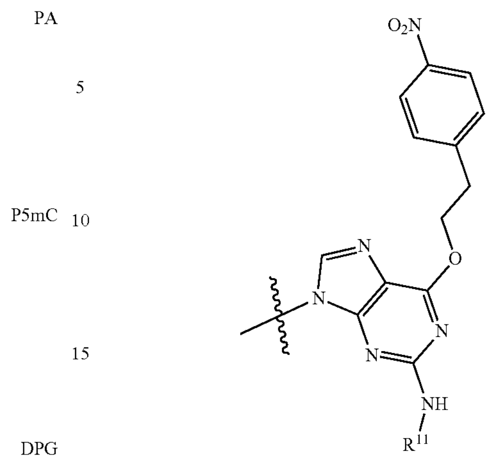

In some embodiments, in Formula X-7 can be hydrogen.

In some embodiments, $T^2$ in Formula X-7 can be trityl or a methoxy substituted trityl group (e.g., MMT, DMT, etc.).

In some embodiments, $T^2$ in Formula X-7 can be an acyl group (e.g., acetyl).

Compounds of Formula X-7 can be prepared by those skilled in the art in view of the present disclosure. An exemplified procedure is also described herein in the Examples section.

An exemplified procedure of converting a compound Formula X-5 into Formula X-6 is described herein, from which those skilled in the art can readily adapt to embodiments of the present disclosure.

It should be noted that the compounds of Formula X-5, X-6, or X-7, as defined herein, are also novel compositions of the present disclosure. Additionally, any of the oligonucleotides produced by the process described herein are also novel compositions of the present disclosure. In some embodiments, the present disclosure further provides a pharmaceutical composition comprising the oligonucleotide produced by the process described herein.

In a further aspect, provided is a process for deprotecting 4-nitrophenethyl (NPE) group from a base-protected phosphorodiamidate morpholino oligomer, which comprises treating the base-protected phosphorodiamidate morpholino oligomer in the presence of an alkaline reagent and a scavenger such as those having 1,3-dicarbonyl moiety. The PMO preferably comprises a targeting base sequence for sequence-specific binding to a target nucleic acid.

In some embodiments of the present disclosure, the process comprises adding the base-protected phosphorodiamidate morpholino oligomer into a mixture of an alkaline reagent and a scavenger.

In some embodiments of the present disclosure, the base-protected phosphorodiamidate morpholino oligomer is, e.g., a compound of Formula X-5 as described in the present disclosure.

The alkaline reagent for deprotecting NPE group is not particularly limited. However, such alkaline reagent, e.g., does not have significant reactivity towards the PMO backbones. The alkaline reagent typically has a pKa suitable for removing an NPE group from a protected base such as protected guanine. In the present disclosure, the alkaline reagent can be an organic alkaline reagent, for example, a basic organic amine having a pKa in water of about 9 or higher, such as about 9-15, about 10-14, about 12, about 13, or about 14. In some embodiments, the alkaline reagent is a basic cyclic amine, such as DBU (1,8-diazabicyclo[5,4,0] undec-7-ene), DBN (1,5-diazabicyclo[4.3.0]non-5-ene), DABCO (1,4-diazabicyclo[2.2.2]octane) or a mixture thereof, e.g., DBU.

The scavenger used for the processes herein include any of those known in the art that can react with 4-nitrostyrene generated from the deprotection of NPE group(s). In some embodiments, the scavenger can have a —SR group or a 1,3-dicarbonyl moiety, e.g., as described herein (e.g., a compound of Formula X-4 as described in the present disclosure). In some preferred embodiments of the present disclosure, the scavenger can be a 1,3-dicarbonyl compound, such as thymine, diethyl malonate or a mixture thereof, e.g., thymine.

In one embodiment, the molar ratio of the alkaline reagent to the NPE group(s) in the base-protected phosphorodiamidate morpholino oligomer can be greater than 1:1, such as 1:1-10:1, 1:2-10:1 or 1.5:1-10:1. In one embodiment, the amount of the alkaline reagent is excessive relative to the NPE groups).

In one embodiment, the scavenger is typically also used in excess. For example, the molar ratio of the scavenger to the NPE group(s) in the base-protected phosphorodiamidate morpholino oligomer is typically more than 1:1, such as 1.2:1, 1.5:1, 2:1, 5:1, 10:1, or any range between the recited values, such as 1:1 to 10:1. In cases where the base-protected phosphorodiamidate morpholino oligomer has one or more bases that can react with 4-nitrostyrene, the amount of scavenger can be further increased, for example, up to 50:1 (or more) of the NPE group(s) of the base-protected phosphorodiamidate morpholino oligomer.

In the present disclosure, the process for deprotecting NPE group can be carried out in the presence of a solvent. The solvent can be any solvent used in the art for deprotecting an NPE group. In the present disclosure, the solvent can be selected from polar aprotic solvents, such as DMF, DMA, DMI, NMP and the like.

In some embodiments of the present disclosure, the process for deprotecting NPE group from a base-protected phosphorodiamidate morpholino oligomer comprises adding a mixture of the base-protected phosphorodiamidate morpholino oligomer in a first solvent to a mixture of an alkaline reagent and a scavenger in a second solvent. The first and second solvents can be the same or different. In some embodiments, the first and second solvent can be selected from polar aprotic solvents, such as DMF, DMA, DMI, NMP and the like. In the mixture of the base-protected phosphorodiamidate morpholino oligomer in the first solvent, the concentration of the base-protected phosphorodiamidate morpholino oligomer can be 0.001 M to 0.1 M, such as 0.01 M to 0.02 M. In the mixture of an alkaline reagent and a scavenger in the second solvent, the concentration of the alkaline reagent can be 0.1 M to 5 M, such as 0.5 M to 1.0 M; and the concentration of the scavenger can be 0.1 M to 5 M, such as 0.5 M-1.5 M, e.g., 0.8 M.

In some embodiments of the present disclosure, the process for deprotecting NPE group from a base-protected phosphorodiamidate morpholino oligomer composes adding a mixture of the base-protected phosphorodiamidate morpholino oligomer in a first solvent to a mixture of an alkaline reagent and a scavenger in a second solvent. The first and second solvents can be the same or different. In some embodiments, the first and second solvent can be selected from polar aprotic solvents, such as DMF, DMA, DMI, NNW and the like. In the mixture of the base-protected phosphorodiamidate morpholino oligomer in the first solvent, the concentration of the base-protected phosphorodiamidate morpholino oligomer can be 0.001 M to 0.1 M, such as 0.01 M to 0.02 M. In the mixture of an alkaline reagent and a scavenger in the second solvent, the concentration of the alkaline reagent can be 0.1 M to 5 M, such as 0.5 M to 1.0 M; and the concentration of the scavenger can be 0.1 M to 5 M, such as 0.5 M-1.5 M, e.g., 0.8 M. In one embodiment, the rate of the addition can be 1-10 mL/min, e.g., 2 mL/min, 3 mL/min, 4 mL/min, 5 mL/min, 6 mL/min, 7 mL/min, 8 mL/min or 9 mL/min.

In some embodiments, the present disclosure provides a process for preparing a phosphorodiamidate morpholino oligomer, which comprises a process for deprotecting NPE group(s) from a base-protected phosphorodiamidate morpholino oligomer as described hereinabove.

Synthesis of oligomers herein is generally performed, as described herein, on a support-medium. In general a first synthon (e.g., a monomer, such as a morpholino subunit) is first attached to a support-medium, and the oligomer is then synthesized by sequentially coupling subunits to the support-bound synthon. This iterative elongation eventually results in a final oligomeric compound. Suitable support-media can be soluble or insoluble, or may possess variable solubility in different solvents to allow the growing support-bound polymer to be either in or out of solution as desired. Traditional support-media are for the most part insoluble and are routinely placed in reaction vessels while reagents and solvents react with and/or wash the growing chain until the oligomer has reached the target length, after which it is cleaved from the support: and, if necessary further worked up to produce the final polymeric compound. More recent approaches have introduced soluble supports including soluble polymer supports to allow precipitating and dissolving the iteratively synthesized product at desired points in the synthesis.

In certain embodiments, a morpholino is conjugated at the 5' or 3' end of the oligomer with a "tail" moiety to increase its stability and/or solubility, Exemplary tails include a short peptide, optionally substituted alkylamino group, optionally substituted heterocyclic group, etc., an acyl group, trityl, etc. In one embodiment, a suitable 5' terminal group is, e.g., a short peptide, optionally substituted alkylamino group, optionally substituted heterocyclic group, etc (e.g., —C(O) $NH_2$) substituted alkyl amine, e.g.,

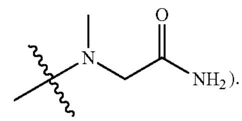 [SMILES: *N(C)CC(N)=O]

In another embodiment, a suitable 3' terminal group is, e.g., hydrogen or a protecting group (e.g., an acyl group, trityl, etc.).

In some embodiments, the present disclosure provides a process for preparing a phosphorodiamidate morpholino oligomer, comprising:

(a) reacting a solid-phase-supported morpholino subunit, having an unprotected ring nitrogen, with a base-protected morpholino subunit monomer, having a protected ring nitrogen and an activated phosphoramidate group on a 5'-exocyclic carbon, thereby forming a phosphorodiamidate linkage between the 5'-exocyclic carbon and the unprotected nitrogen;

(b) deprotecting the protected nitrogen, to form an unprotected nitrogen;

(c) repeating steps (a) and (b) one or more times with further base-protected morpholino subunit monomers to obtain a base-protected morpholino modified solid support; and (d) conducting a three steps of cleavage and deprotection to obtain the phosphorodiamidate morpholino oligomer; the three steps of cleavage and deprotection comprises a process for deprotecting NPE group from a base-protected phosphorodiamidate morpholino oligomer as described above;

wherein at least one of the base-protected morpholino subunit monomers is a protected guanine morpholino compound having the structure (M):

(M)

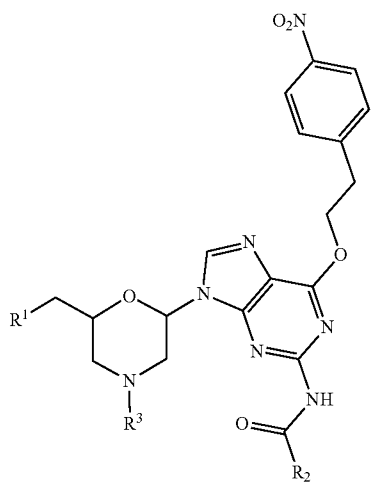

$R^1$ is a chlorophosphoramidate group;

$R^2$ is lower alkyl, monocyclic arylmethyl, or monocyclic (aryloxy)methyl;

$R^3$ is triarylmethyl.

Examples for triarylmethyl protecting groups for the morpholino ring nitrogen ($R^3$) can be triphenylmethyl (trityl), 4-methyltrityl, 4,4'-dimethyltrityl, 4,4',4"-trimethyltrityl, monomethoxytrityl (e.g., 4-methoxytrityl) or dimethoxytrityl 4,4'-dimethoxytrityl).

$R^1$ can be $—O—P(=O)—N(CH_3)_2Cl$.

$R^2$ can be benzyl or $—CH(CH_3)_2$.

In one aspect, provided herein is a process for preparing a compound of formula (II), which comprises contacting compound (E) with a deblocking agent to obtain the compound of formula (II);

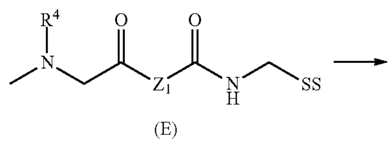

(E)

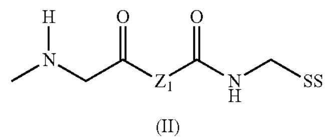

(II)

wherein SS is a support-medium, $Z_1$ is

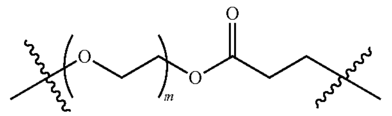

the oxygen end is connected to the sarcosine unit, m is 1, 2, 3, 4 or 5, $R^4$ is Tr (triphenyl ethyl) or a derivative thereof, such as Tr (triphenylmethyl), MMTr (p-methoxyphenyldiphenylmethyl) or DMTr (di-(p-methoxyphenyl)phenylmethyl). In a preferred embodiment, m is 3, and $R^4$ is Tr (triphenylmethyl).

In one embodiment, the process for preparing a compound of formula (II) further comprises the step of contacting the deblocked compound with a neutralization agent.

In another aspect, provided herein: is a process for preparing a compound of formula (III), which comprises coupling a compound of formula (II) with a compound of formula (G) to obtain the compound of formula (III);

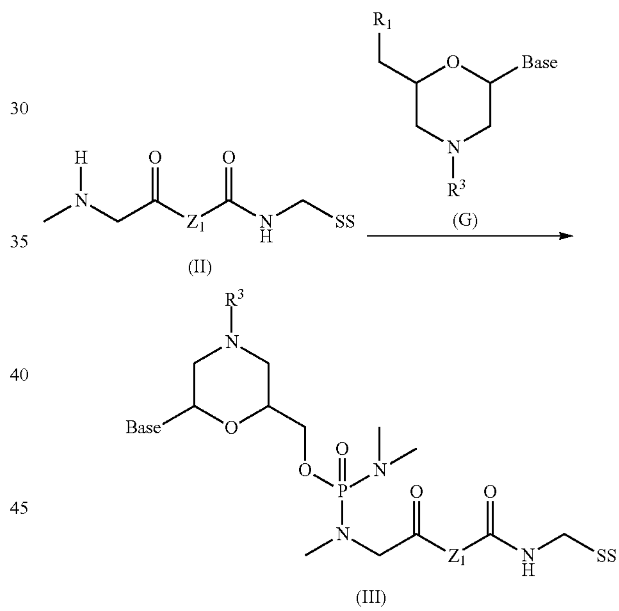

Base is selected from an optionally protected nucleic acid base, such as PC, T, PA, P5mC, U, I, PG, DPG or NPEG; G (guanine), C (cytosine), A (adenine), U (uracil), and T (thymine), modified analogs thereof, and protected derivatives thereof, e.g., an optionally protected nucleic acid base, such as PC, T, PA, P5mC, U, I, PG, DPG or NPEG;

PC

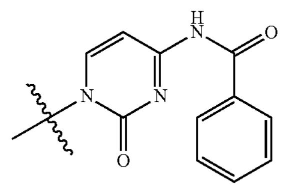

-continued

T

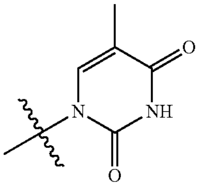

PA

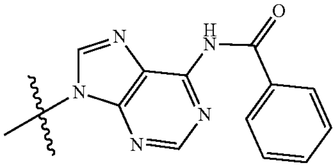

P5mC

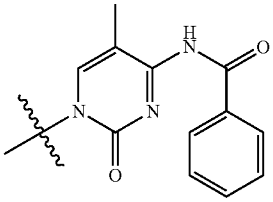

DPG

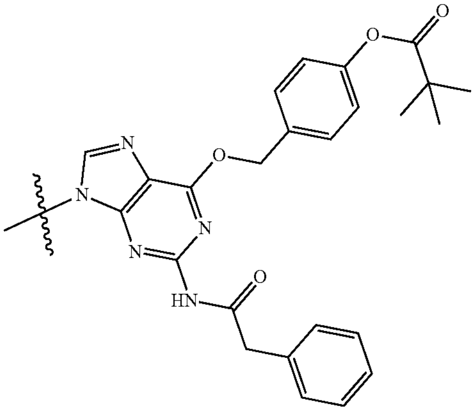

U

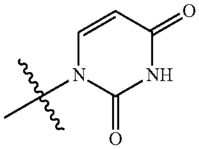

I

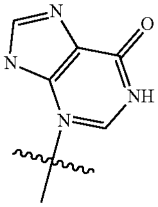

PG

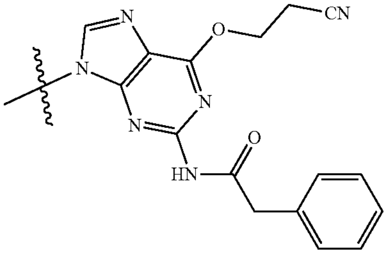

-continued

NPEG

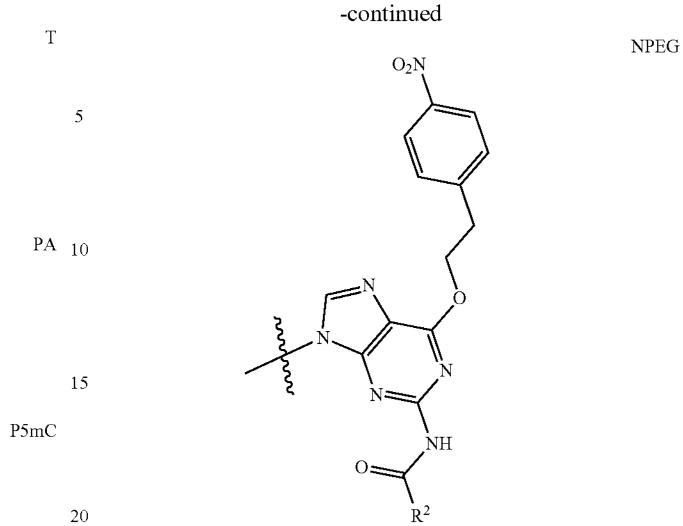

the definitions of SS, $Z_1$, $R^1$, $R^2$ and $R^3$ are as described in the present disclosure.

In one embodiment, the process for preparing a compound of formula (III) further comprises contacting the compound of formula (II) with a capping agent.

In another embodiment, the compound of formula (II) is obtained from the process as defined above.

In another aspect, provided herein is a process for preparing a compound of formula (IV), which comprises the sequential steps of:

(i) coupling a compound of formula (II) with a compound of formula (G) to obtain the compound of formula (III);

(ii) performing n−1 iterations of the sequential steps of:

(ii-1) contacting the product obtained by the immediately prior step with a deblocking agent; and (ii-2) coupling the compound obtained by the immediately prior step with a compound of formula (G) to form the compound of formula (IV);

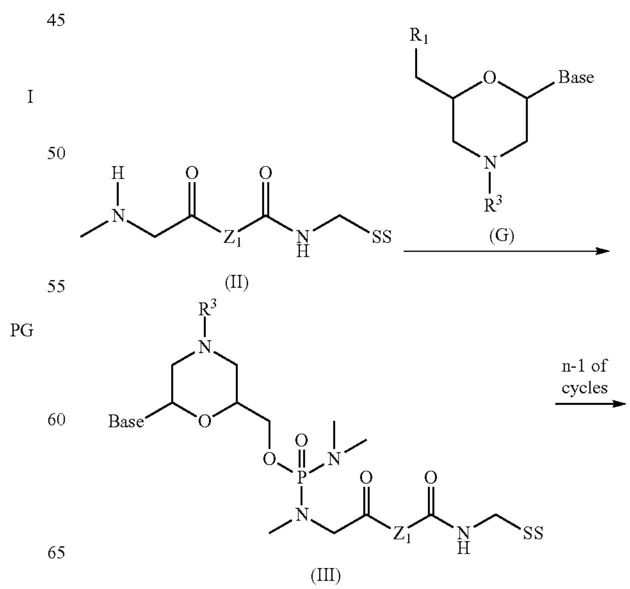

(II) (G) (III)

-continued

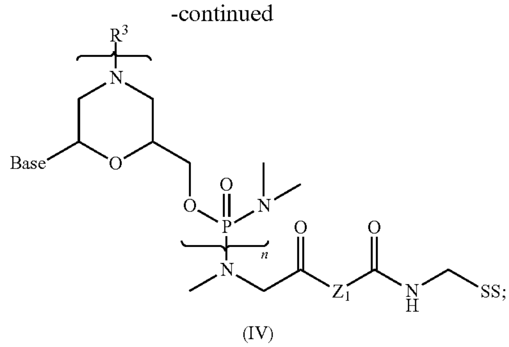

(IV)

optionally at least one of the bases is NPEG;

NPEG

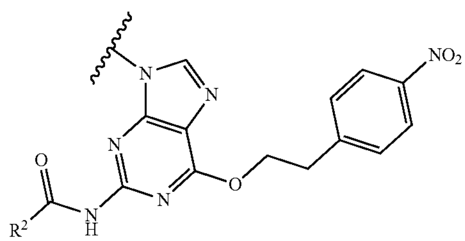

wherein the definitions of SS, $Z_1$, $R^1$, $R^2$ and $R^3$ are as described in the present disclosure; n is an integer from 10 to 40, e.g., n is an integer from 20-30, such as 25;

Base at each occurrence is independently a base selected from an optionally protected nucleic acid base, such as such as PC, T, PA, P5mC, U, I, PG, DPG or NPEG; G (guanine), C (cytosine), A (adenine), U (uracil), and T (thymine), modified analogs thereof, and protected derivatives thereof, e.g., an optionally protected nucleic acid base, such as PC, T, PA, P5mC, U, I, PG, DPG or NPEG.

In one embodiment, step (ii-1) further comprises the step of contacting the deblocked compound with a neutralization agent.

In another embodiment, step (ii-2) further comprises contacting the compound obtained by immediately prior step with a capping agent.

In yet another aspect, provided herein is a process for preparing a compound of formula (V) which comprises contacting a compound of formula (IV) with a deblocking agent to obtain the compound of formula (V);

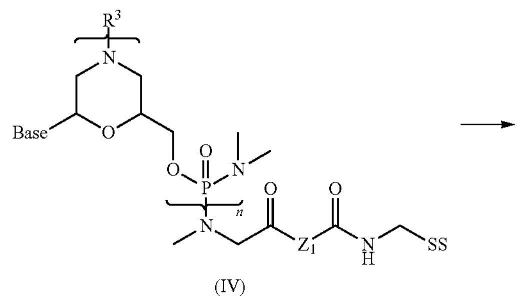

(IV)

-continued

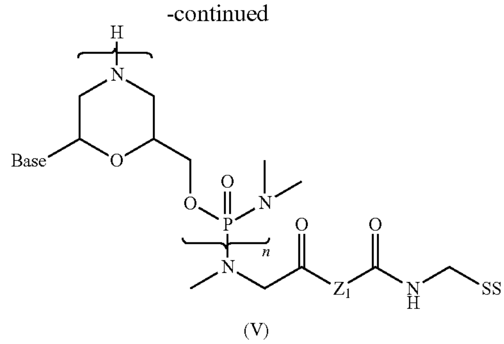

(V)

wherein the definitions of SS, $Z_1$, Base, $R^3$ and n are as described in the present disclosure.

In one embodiment, the process for preparing a compound of formula (V) further comprises the step of contacting the deblocked compound with a neutralization agent.

In still another aspect, provided is a process for preparing a compound of formula (VI), which comprises contacting a compound of formula (V) with a cleaving agent to obtain the compound of formula (VI);

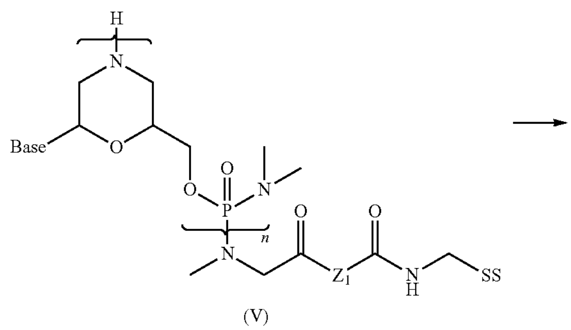

(V)

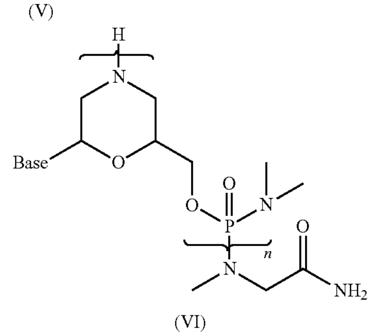

(VI)

wherein the definitions of SS, $Z_1$, Base, $R^3$ and n are as described in the present disclosure.

In another aspect, provided herein is a process for preparing a phosphorodiamidate morpholino oligomer, which comprises:

(a) contacting a compound of formula (VI) with a deprotecting agent; and (h) optionally, conducting an aminolysis reaction on the compound obtained by the immediately prior step to obtain the phosphorodiamidate morpholino oligomer;

(VI)

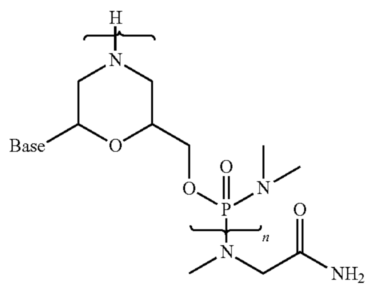

wherein the definitions of Base and n are as described in the present disclosure.

In one embodiment, each process (step) is performed in the presence of at lead one solvent.

In another embodiment, the neutralization agent is in a solution comprising dichloromethane and isopropyl alcohol.

In yet another embodiment, the neutralization agent is a monoalkyl, dialkyl, or trialkyl amine.

In still another embodiment, the neutralization agent is N,N-diisopropylethylamine.

In a preferred embodiment, the neutralization agent used in each process (step) is 5% diisopropylethylamine in 25% isopropanol/dichloromethane.

In another embodiment, the compound of formula (G) is in a solution comprising ethylmorpholine and dimethylimidazolidinone.

In a further embodiment, the compounds of formula (G) is selected from PMO-NPEG monomer, PMO-PA monomer, PMO-PC monomer and PMO-T monomer;

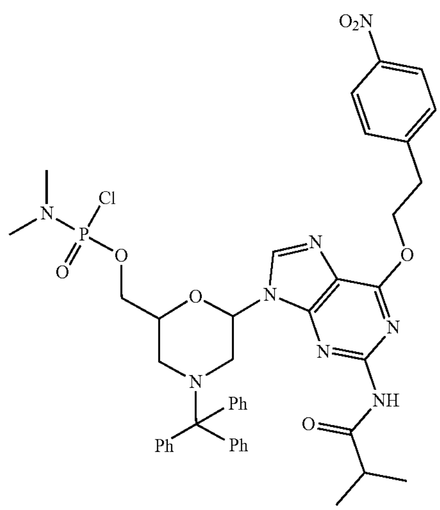

PMO-NPEG monomer

-continued

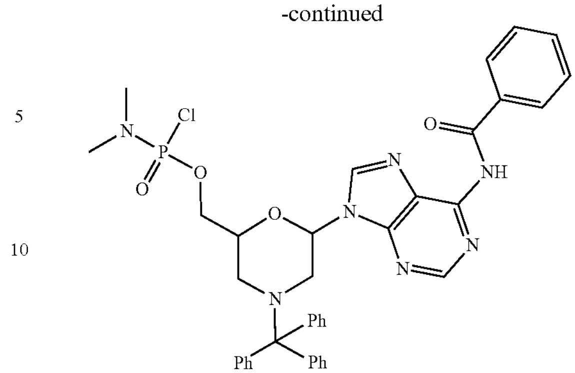

PMO-PA monomer

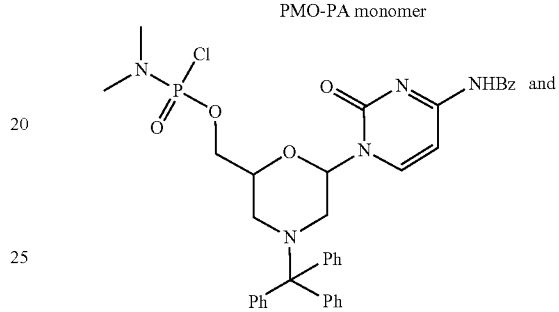

and

PMO-PC monomer

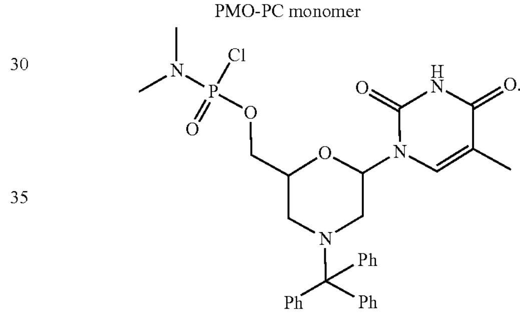

PMO-T monomer

In some embodiments, the processes of the present disclosure can be performed in a continuous flow mode or a discontinuous flow mode known in the art. In some embodiments, the processes of the present disclosure can be performed in a Customized Peptide Batch Reactor.

In still another aspect, provided is a process for preparing compound (E), which comprises contacting; compound (B) with compound (S) to obtain the compound (E);

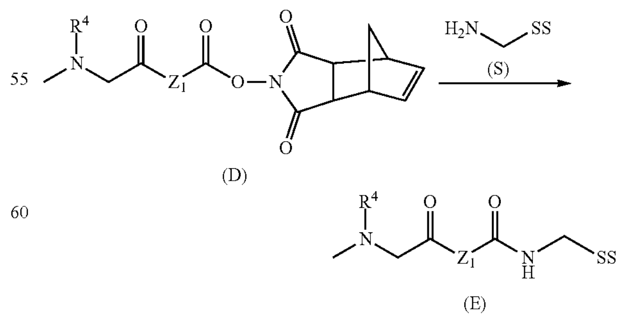

wherein the definitions of SS. $Z_1$ and $R^4$ are as defined in the present disclosure.

In the process for preparing compound (E), compound (S) may need to be activated before use, wherein activation of compound (S) may comprise the following steps: suspending compound (S) into a solvent and swelling, then removing the solvent and washing with a chlorinated hydrocarbon solvent and a mixture of a base in a solvent successively.

In the activation of compound (S), the solvent for suspending compound (S) can be selected from polar aprotic solvents, such as alkanone solvents, e.g., NMP. The amount of the solvent may not specifically limited. The volume-mass ratio of the solvent to compound (S) can be 10 mL/g-30 mL/g. The operation for removing the solvent can be filtration. The chlorinated hydrocarbon solvent can be DCM. The base in the mixture can be an organic base, such as DIPEA. The solvent in the mixture can be an alcohol solvent (e.g., IPA), a chlorinated hydrocarbon solvent (e.g., DCM) or a combination thereof, more preferably a combination of an alcohol solvent and a chlorinated hydrocarbon solvent (e.g., a combination of IPA and DCM, the volume ratio can be 1:1-1:5, 1:3). In the mixture, the mass percentage of the base can be 1%-10%, e.g., 5%, the % represents for the mass of the base in the total mass of the mixture.

The process for preparing compound (E) can be carried out in a solvent. The solvent can be selected from polar aprotic solvents, such as alkanone solvents, amide solvents or a mixture thereof, e.g., NMP, DMI, DMF or a mixture thereof. The amount of the solvent may not specifically limited. The volume-mass ratio of the solvent to compound (S) can be 10 mL/g-30 mL/g.

In the process for preparing compound (E), the molar ratio of compound (D) and compound (S) can be 1:1-1:3.

In the process for preparing compound (E), the temperature for reaction can be 20-50° C., such as 40-45° C. The progress of reaction can be monitored using conventional detection methods in the art (such as TLC, HPLC, GC or NMR). The disappearance of compound (D) is generally seen as the completion of the reaction. And the time for reaction can be 24-48 hours.

In a preferred embodiment, the process for preparing compound (E) preferably comprises adding a solution of compound (D) in the solvent to a suspension of compound (S) in the solvent to carry out a reaction.

In the process for preparing compound (E), the post-treatment can be a conventional post treatment for such reactions in the art. In the present disclosure, the post-treatment preferably comprises filtering the resulting mixture and then washing the filter cake with a solvent (such as an alkanone solvent, a chlorinated hydrocarbon solvent or a combination thereof; the alkanone solvent can be NMP; the chlorinated hydrocarbon solvent can be DCM; when the solvent is a combination of an alkanone solvent and a chlorinated hydrocarbon solvent, the volume ratio thereof can be 1:14:10), followed by addition of a solution of NEM (0.2-1.0 M) in a solvent (such as an alkanone solvent; e.g., NMP, the volume-mass ratio of the solvent to compound (S) can be 50 mL/g-200 mL/g) and a solution of $Bz_2O$ (0.2-1.0 M) in a solvent (such as an alkanone solvent; e.g., NMP; the volume-mass ratio of the solvent to compound (S) can be 50 mL/g-200 mL/g) successively, and conducting a capping reaction, after the completion of the capping reaction, the obtained mixture is filtered and washed with a solvent (such as a chlorinated hydrocarbon solvent, e.g., DCM; the volume-mass ratio of the solvent to compound (S) can be 100 mL/g-300 mL/g) and then drying to obtain compound (E).

In a preferred embodiment of the present disclosure, compound (S) is aminomethyl polystyrene resin, which is available from Xi'an Lanxiao Technology Co., Ltd.

In a preferred embodiment of the present disclosure, the process for preparing compound (E) can further comprise a process for preparing compound (D), which comprises in a solvent, contacting compound (C) with compound (SM4) in the presence of a catalyst, a base and a condensing agent to obtain compound (D);

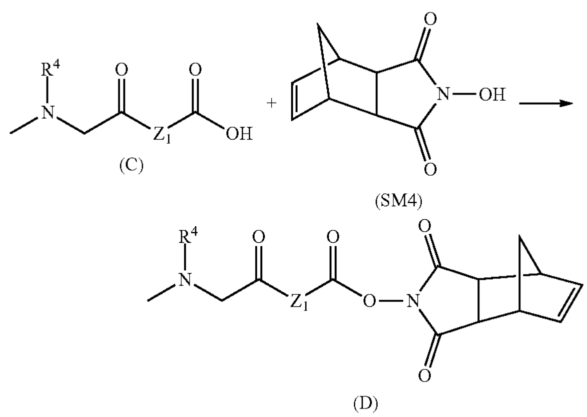

(C) (SM4)

(D)

wherein the definitions of $Z_1$ and $R^4$ are as defined in the present disclosure.

In the process for preparing compound (D), the catalyst is a conventional catalyst for such reactions in the art. In the present disclosure, the catalyst can be DMAP. The molar ratio of the catalyst to compound (C) can be 0.01:1-0.5:1, such as 0.33:1.

In the process for preparing compound (D), the base is a conventional base for such reactions in the art. In the present disclosure, the base can be an organic base, such as an organic amine, e.g., DIPEA. The amount of the base is a conventional amount for such reactions in the art. In the present disclosure, the molar ratio of the base to compound (C) can be 1:-3:1; such as 2.5:1.

In the process for preparing compound (10), the condensing agent is a conventional condensing agent for such reactions in the art. In the present disclosure, the condensing agent can be EDCI, DCC, DIC or a mixture thereof. The amount of the condensing agent is a conventional amount for such reactions in the art. In the present disclosure, the molar ratio of the condensing agent to compound (C) can be 1:1-2:1, such as 1.11.

In the process for preparing compound (D), the molar ratio of compound (C) and compound (SM4) can be 1:1-1:2, such as 1:1.02.

In the process for preparing compound (D), the solvent be a conventional solvent for such reactions in the art. In the present disclosure, the solvent can be a chlorinated hydrocarbon solvent, such as DCM. The volume-mass ratio of the solvent to compound (C) can be 10 mL/g-20 mL/g, such as 10 mL/g.

In the process for preparing compound (D), the temperature for reaction can be 20-30° C. The progress of reaction can be monitored using conventional detection methods in the art (such as TLC, HPLC, GC or NMR). The disappearance of compound (C) is generally seen as the completion of the reaction.

In a preferred embodiment, the process for preparing compound (D) comprises adding compound (SM4), the catalyst, the base and the condensing agent to a solution of compound (C) in the solvent to carry out a reaction.

In the process for preparing compound (D), the post-treatment can be a conventional post treatment for such reactions in the art. In the present disclosure, the post-treatment preferably comprises washing the reaction mixture with citric acid (e.g., 10% citric acid solution) and brine successively, and the organic layer is concentrated to dryness to obtain compound (D), In a preferred embodiment of the present disclosure, the process for preparing compound (E) can further comprise a process for preparing compound (C), which comprises contacting compound (B) with compound (SM3) in a solvent to obtain compound (C);

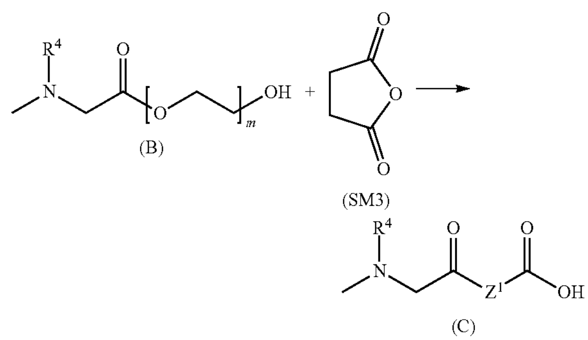

(B) (SM3) (C)

wherein m is an integer from 1 to 5, the definition of $R^4$ is as defined in the present disclosure.

In the process for preparing compound (C), the molar ratio of compound (B) to compound (SM3) can be 1:1-1:2, such as 1:2.

In the process for preparing compound (C), the solvent can be a conventional solvent for such reactions in the art. In the present disclosure, the solvent can be an ether solvent, such as THF. The volume-mass ratio of the solvent to compound (B) can be 10-20 mL/g, such as 10 mL/g.

In the process for preparing compound (C), the temperature for reaction can be 20-55° C. The progress of reaction can be monitored using conventional detection methods in the art (such as TLC, HPLC, GC or NM). The disappearance of compound (B) is generally seen as the completion of the reaction.

In a preferred embodiment, the process for preparing compound (C) preferably comprises adding compound (SM3) to a solution of compound (B) in the solvent to carry out a reaction.

In the process for preparing compound (C), the post-treatment can be a conventional post treatment for such reactions in the art. In the present disclosure, the post-treatment comprises adjusting the pH of the reaction mixture to about 8.5 with $NaHCO_3$ aqueous solution (e.g., 10% $NaHCO_3$ aqueous solution), then adding an ether solvent (e.g MTBE), the pH of the resulting aqueous layer is adjusted to 3-5 with citric acid solution (20% citric acid solution), then extracted with a chlorinated hydrocarbon solvent (e.g., Devi) and washed with $Na_2SO_4$ aqueous solution (e.g., 10% $Na_2SO_4$ aqueous solution), and the resulting organic layer is concentrated to obtain compound (C).

In a preferred embodiment of the present disclosure, the process for preparing compound (E) can further comprise a process for preparing compound (B), which comprises in a solvent, contacting compound (A) with compound (SM2) in the presence of a base to obtain compound (B),

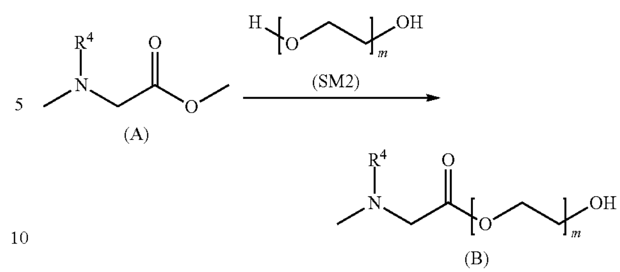

(A) (SM2) (B)

wherein m is an integer from 1 to 5, the definition of $R^4$ is as defined in the present disclosure.

In the process for preparing compound (B), the base is a conventional base for such reactions in the art. In the present disclosure, the base can be a metal hydride, such as NaH. The molar ratio of the base to compound (SM2) can be 0.01:1-1:1, such as 0.01:1.

In the process for preparing compound (B), the molar ratio of compound (A) to compound (SM2) can be 1:5-1:20, such as 1:10.

In the process for preparing compound (B), the solvent can be a conventional solvent for such reactions in the art. In the present disclosure, the solvent can be an alkanone solvent; e.g., NNW The amount of the solvent may not be specifically limited. The volume-mass ratio of the solvent to compound (A) can be 15 mL/g-25 mL/g, such as 20 mL/g.

In the process for preparing compound (B), the temperature for reaction can be 20-30° C. The progress of reaction can be monitored using conventional detection methods in the art (such as TLC, HPLC, GC or NMR). The disappearance of compound (A) is generally seen as the completion of the reaction.

In a preferred embodiment, the process for preparing compound (B) preferably comprises adding the base to a solution of compound (SM2) in the solvent under stirring, then adding compound (A) to carry out a reaction, more preferably comprises adding the base to a solution of compound (SM2) in the solvent at 20-30° C., then the obtained mixture is stirred at 20-30° C. for 10-30 minutes, then adding compound (A) to carry out a reaction.

In the process for preparing compound (B), the post-treatment can be a conventional post treatment for such reactions in the art. In the present disclosure, the post-treatment comprises adding water and an organic solvent for extraction (e.g., a chlorinated hydrocarbon solvent, an ether solvent or a mixture thereof, preferably a mixture solvent of DCM, and MTBE) into the reaction mixture, then washing the obtained organic layer with brine, and the resulting organic layer is concentrated and purified (e.g., silica gel column) to obtain compound (B).

In a preferred embodiment of the present disclosure, the process for preparing compound (E) can further comprise a process for preparing compound (A), which comprises in a solvent, contacting compound (SM1) with $R^4Cl$ in the presence of a base to obtain compound (A);

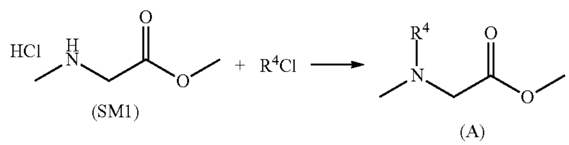

(SM1) (A)

wherein $R^4$ is as defined in the present disclosure.

In the process for preparing compound (A), the base is a conventional base for such reactions in the art. In the present disclosure, the base can be an organic base, such as an organic amine, e.g., DIPEA. The amount of the base is a conventional amount for such reactions in the art. In the present disclosure, the molar ratio of the base to $R^4Cl$ can be 1:1-3:1, such as 1.5:1.

In the process for preparing compound (A), the molar ratio of the compound (SM1) to $R^4Cl$ can be 1:1-1:3, such as 1:2.

In the process for preparing compound (A), the solvent is a conventional solvent for such reactions in the art. In the present disclosure, the solvent can be selected from amides solvent, such as amide solvents, alkanone solvents, chlorinated hydrocarbon solvent, or a mixture thereof, e.g., DMF, DCM, NMP or a mixture thereof. The amount of the solvent may not be specifically limited. In the present disclosure, the volume-mass ratio of the solvent to the compound (SM1) can be 10 mL/g-30 mL/g, such as 10 mL/g.

In the process for preparing compound (A), the temperature for reaction can be 20-25° C. The progress of reaction can be monitored using conventional detection methods in the art (such as TLC, HPLC, GC or NMR). The disappearance of the compound (SM1) is generally seen as the completion of the reaction.

In a preferred embodiment, the process for preparing compound (A) preferably comprises adding the base and $R^4Cl$ successively to a solution of compound (SM1) in the solvent to carry oat a reaction.

In the process for preparing compound (A), the post-treatment can be a conventional post treatment for such reactions in the art. In the present disclosure, the post-treatment comprises adding water and an organic solvent for extraction (e.g., an ester solvent, preferably EtOAc) into the reaction mixture, then washing the obtained organic layer with NaCl aqueous solution (e.g., 20% NaCl aqueous solution), and the resulting organic layer is concentrated and purified (e.g., silica gel column) to obtain compound (A).

In still another aspect, provided is a compound (E):

(E)

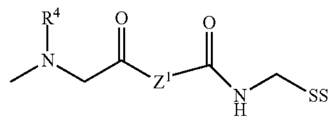

wherein $Z_1$ is

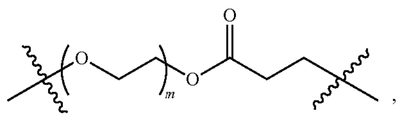

the oxygen end is connected to the sarcosine unit, m is 1, 2, 3, 4, or 5, the definitions of SS and $R^4$ are as defined in the present disclosure.

In a further aspect, provided is use of the compound (E) as described in the present disclosure in the preparation of oligonucleotides such as phosphorodiamidate morpholino oligomers (PMOs).

As described herein, it was discovered that oligonucleotides can be prepared in high yield and purity using an NPE protected guanine monomeric unit. It was also discovered that the deprotection of the NPE group from a non-solid support bound oligonucleotide can be carried out in high efficiencies with minimal NPE adducts (impurities).

Definitions

Unless defined otherwise, all technical and scientific terms used herein have the same meaning as commonly understood by one of ordinary skill in the art to which the disclosure pertains.

It is understood that wherever embodiments, are described herein with the language "comprising" otherwise analogous embodiments, described in terms of "containing" "consisting of" and/or "consisting essentially of" are also provided. However, when used in the claims as transitional phrases, each should be interpreted separately and in the appropriate legal and factual context (e.g., in claims, the transitional phrase "comprising" is considered more of an open-ended phrase while "consisting of" is more exclusive and "consisting essentially of" achieves a middle ground).

As used herein, the singular form "a", "an", and "the", includes plural references unless it is expressly stated or is unambiguously clear from the context that such is not intended.

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

When a range of values is listed, it is intended to encompass each value and sub-range within the range. For example "$C_{1\ 6}$" is intended to encompass $C_1$, $C_2$, $C_3$, $C_4$, $C_5$, $C_6$, $C_{1\ 6}$, $C_{1\ 5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

A "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred morpholino oligomer is composed of "morpholino subunit" structures, such as shown below, which in the oligomer are preferably linked together by (thio) phosphorodiamidate linkages, joining the morpholino nitrogen of one subunit to the 5' exocyclic carbon of an adjacent subunit. Each subunit includes a purine or pyrimidine base-pairing moiety Base which is effective to bind, by base-specific hydrogen bonding, to a base in a polynucleotide.

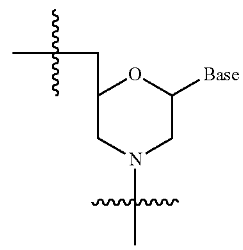

A "phosphorodiamidate" group comprises phosphorus having two attached oxygen atoms and two attached nitrogen atoms, and herein may also refer to phosphorus having one attached oxygen atom and three attached nitrogen atoms. In the intersubunit linkages of the oligomers descried herein, one nitrogen is typically pendant to the backbone chain, and the second nitrogen is the ring nitrogen m a morpholino ring structure: as shown in formula (a1) below. Alternatively or in addition, a nitrogen may be present at the 5'-exocyclic carbon, as shown in formulas (b1) and (c1) below.

(a1)

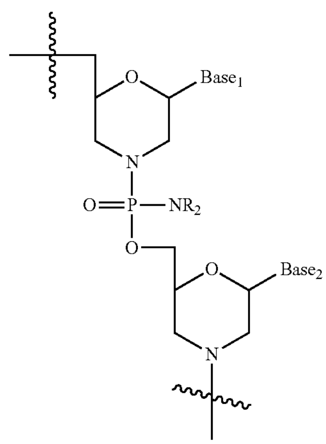

(b1)

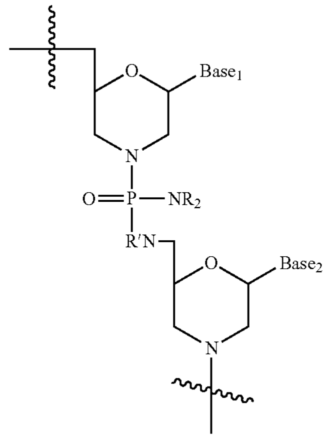

(c1)

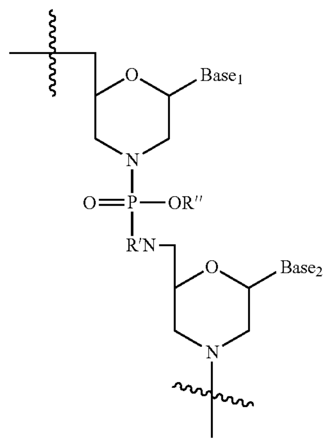

The Base1 and Base2 may be the same or different, the definitions of which are same as the base as described in the disclosure.

In a thiophosphorodiamidate linkage, one oxygen atom, typically an oxygen pendant to the backbone in the oligomers described herein, is replaced with sulfur.

In a preferred embodiment, the phosphorodiamidate morpholino oligomer refers to a phosphorodiamidate morpholino oligomer of the following general structure:

(a11)

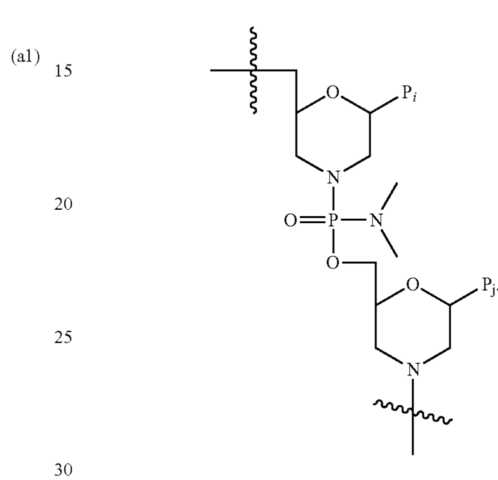

A "solid-phase-supported morpholino subunit" can be the first or any subsequent morpholino subunit monomer incorporated into a morpholino oligomer by solid-phase step-wise synthesis as described herein. The subunit is attached to the solid support, or to a growing oligomer chain on the solid support, via its 5' exocyclic carbon. "Base-protected" refers to protection of the base-pairing groups, e.g., purine or pyrimidine bases, on the morpholino subunits with protecting groups suitable to prevent reaction or interference of the base-pairing groups during stepwise oligomer synthesis.

An "activated phosphoramidate group" is typically a chlorophosphoramidate group, having substitution at nitrogen which is desired in the eventual phosphoramidate linkage in the oligomer. An example is (dimethylamino)chlorophosphoramidate, i.e. —O—P(=O)($NMe_2$)Cl.

"Base-protected" or "base protection" refers to protection of the base-pairing groups, e.g., purine or pyrimidine bases, on the morpholino subunits with protecting groups suitable to prevent reaction or interference of the base-pairing groups during stepwise oligomer synthesis. In a preferred embodiment, at least one of the base-protected morpholino subunit monomers is derived from a protected guanine morpholino compound having the structure (M):

(M)

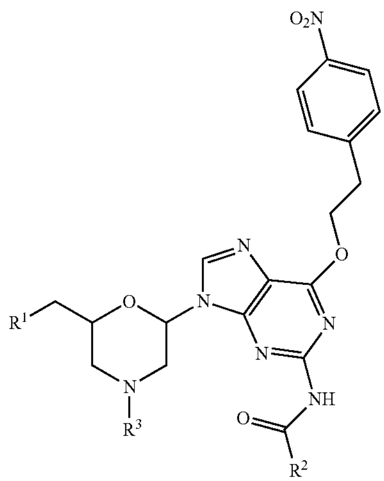

the definitions of $R^1$, $R^2$ and $R^3$ are as described in the present disclosure.

The "nucleic acid base" is not particularly limited as long as it can be used for the synthesis of nucleic acid and includes, for example, a pyrimidine base such as cytosyl group, uracil group, thyminyl group and the like, and a purine base such as adenyl group, guanyl group and the like. The "optionally protected nucleic acid base" means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of die morpholine ring nitrogen atom of the morpholino nucleotide is preferable. The "amino-protecting group" is not particularly limited, specific examples of the "amino-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, (phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. To some cases, the carbonyl-protecting group does not need to be particularly introduced. Moreover in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a hypoxanthinyl group, etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, monoalkylamino, dialkylamino, carboxy, cyano, nitro etc.) at any position(s), are also encompassed in the "nucleic acid base".

"Lower alkyl" refers to an alkyl radical of one to six carbon atoms, as exemplified by methyl, ethyl, n-butyl, i-butyl, t-butyl, isoamyl, n-pentyl, and isopentyl. In selected embodiments, a "lower alkyl" group has one to four carbon atoms, or 1-2 carbon atoms; i.e. methyl or ethyl.

The term "support-bound" refers to a chemical entity that is covalently linked to a support-medium.

The term "support-medium" refers to any material including, for example, any particle, bead, or surface, upon which an oligomer can be attached or synthesized upon, or can be modified for attachment or synthesis of an oligomer. Representative substrates include, but are not limited to, inorganic supports and organic supports such as glass and modified or functionalized glass, plastics (including acrylics, polystyrene and copolymers of styrene and other materials, polypropylene, polyethylene, polybutylene, polyurethanes, TEFLON, etc), polysaccharides, nylon or nitrocellulose, ceramics, resins, silica or silica-based materials including silicon and modified silicon, carbon, metals, inorganic glasses, plastics, optical fiber bundles, and a variety other polymers. Particularly useful support-medium and solid surfaces for some embodiments are located within a flow cell apparatus. In some embodiments of the processes described herein, the support-medium comprises polystyrene with 1% crosslinked divinylbenzene. In other embodiments of the processes described herein, the support-medium is aminomethyl polystyrene resin (e.g., purchased from Xi'an Lanxiao Technology Co., Ltd., and the loading of which is, for example, 1 mmol/g).

In some embodiments, representative support-medium comprise at least one reactive site for attachment or synthesis of an oligomer. For example, in some embodiments, a support-medium of the disclosure comprises one or more terminal amino or hydroxyl groups capable of forming a chemical bond with an incoming subunit or other activated group for attaching or synthesizing an oligomer.

The term "flow cell apparatus" refers to a chamber comprising a surface (e.g., solid surface) across which one or more fluid reagents (e.g., liquid or gas) can be flowed.

The term "deblocking agent" refers to a composition e.g., a solution) comprising a chemical acid or combination of chemical acids for removing protecting groups. Exemplary chemical acids used in deblocking agents include halogenated acids, e.g., chloroacetic acid, dichloroacetic acid, trichloroacetic acid, fluoroacetic acid, difluoroacetic acid, and trifluoroacetic acid. In some embodiments, a deblocking agent removes one or more trityl groups from, for example, an oligomer, a support-bound oligomer, a support-bound subunit, or other protected nitrogen or oxygen moiety. In another embodiment, the deblocking agent used in each process (step) is a solution comprising 4-cyanopyridine, dichloromethane, trifluoroacetic acid, trifluoroethanol, and water or a solution comprising 4-cyanopyridinium trifluoroacetate, trifluoroethanol, dichloromethane and ethanol. In a preferred embodiment; the deblocking agent used in each process (step) is 2% 4-cyanopyridinium trifluoroacetate (CYTFA) (w/v) in 20% trifluoroethanol/dichloromethane with 1% ethanol.

The terms "halogen" and "halo" refer to an atom selected from fluorine, chlorine, bromine, and iodine.

The term "capping agent" refers to an acid anhydride (e.g., benzoic anhydride, acetic anhydride, phenoxyacetic anhydride, and the like) useful for blocking a reactive cite of, for example, a support-medium forming a chemical bond with an incoming subunit or other activated group. In an embodiment, the capping agent is in a solution comprising ethylmorpholine and methylpyrrolidinone. In a preferred embodiment, the capping agent of the present disclosure comprises capping A and capping B, wherein capping A is a solution of NEM in NMP, and capping B is a solution of the capping agent in NMP.

The term "cleavage agent" refers to a composition (e.g., a liquid solution or gaseous mixture) comprising a chemical base (e.g., ammonia or 1,8-diazabicycloundec-7-ene) or a combination of chemical bases useful for cleaving, for example, a support-hound oligomer form a support-medium. In still another embodiment, the cleavage agent is in a solution comprising N-methyl-2-pyrrolidone.

The term "deprotecting agent" refers to a composition (e.g., a liquid solution or gaseous mixture) comprising a chemical base (e.g., ammonia, 1,8-diazabicycloundec-7-ene or potassium carbonate) or a combination of chemical bases useful for removing protecting groups. For example, a deprotecting agent, in some embodiments, can remove the base protection from, for example, a morpholino subunit, morpholino subunits of a morpholino oligomer, or support bound versions thereof. In another embodiment, the cleavage agent comprises dithiothreitol and 1,8-diazabicyclo[5,4,0]undec-7-ene.

The term "solvent" refers to a component of a solution or mixture in which a solute is dissolved. Solvents may be inorganic or organic (e.g., acetic acid, acetone, acetonitrile, acetyl acetone, 2-aminoethanol, aniline, anisole, benzene, benzonitrile, benzyl alcohol, 1-butanol, 2-butanol, i-butanol, 2-butanone, t-butyl alcohol, carbon disulfide, carbon tetrachloride, chlorobenzene, chloroform, cyclohexane, cyclohexanol, cyclohexanone, di-n-butyl-phthalate, 1,1-dichloroethane, 1,2-dichloroethane, diethylamine, di ethylene glycol, diglyme, dimethoxyethane, N,N-dimethylaniline, dimethylformamide (DMF), dimethylacetamide (DMA), 1,3-dimethyl-2-imidazolidinone (DMI), 1-methyl-2-pyrrolidinone (NMP), dimethylphthalate, dimethylsulfoxide, dioxane, ethanol, ether, ethyl acetate, ethyl acetoacetate, ethyl benzoate, ethylene glycol, glycerin, heptane, 1-heptanol, hexane, 1-hexanol, methanol, methyl acetate, methyl t-butyl ether, methylene chloride, 1-octanol, pentane, 1-pentanol, 2-pentanol, 3-pentanol, 2-pentanone, 3-pentanone, 1-propanol, 2-propanol, pyridine, tetrahydrofuran, toluene, water, p-xylene).

In the present disclosure, G, C, A, U and T are guanine, cytosine, adenine, uracil, and thymine, respectively.

G

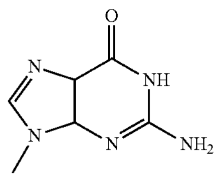

C

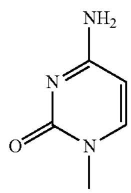

-continued

A

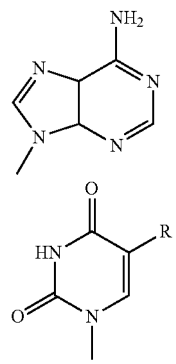

U: R = H (RNA)
T: R = $CH_3$ (DNA)

Abbreviation

DMF represents for N, N-dimethylformamide,
DIPEA represents for N, N-diisopropylethylamine;
TrCl represents for triphenylmethyl chloride;
TLC represents for thin layer chromatography;
EtOAc represents for ethyl acetate;
NaCl represents for sodium chloride;
DBU represents for 1,8-diazabicyclo[5,4,0]undec-7-ene;
DBN represents for 1,5-diazabicyclo[4.3.0]non-5-ene;
DABCO represents for 1,4-diazabicyclo[2.2.2]octane;
NMP represents for 1-methyl-2-pyrrolidinone;
NPE represents for 4-nitrophenethyl (NPE) group;
IPC represents for In-Process Control;
UV represents for ultraviolet;
CYTFA represents for 4-cyanopyridinium trifluoroacetate;
Vol. (vol.) represents for volume;
DCM represents for dichloromethane;
MTBE represents for methyl tert-butyl ether;
DMAP represents for dimethylaminopyridine;
EDCI represents for 1-ethyl-3-(3-dimethylaminopropyl) carbodiimide hydrochloride;
IPA represents for isopropyl alcohol;
NEM represents for N-Ethyl morpholine;
$Bz_2O$ represents for benzoic anhydride;
DMI represents for 1,3-dimethyl-2-imidazolidinone;
PMO represents for phosphorodiamidate morpholino oligomer;
CAP A represents for Capping A;
CAP B represents for Capping B;
"a M" represents for "a mol/L", wherein a is digital;
min represents for minute(s).

EXAMPLES

The following examples thither illustrate the present invention, but the present invention is not limited thereto. If the temperature is not limited in the operation of the examples, it means that the operation is performed at room temperature.

Example 1 Synthesis of Compound (E)

Synthetic route:

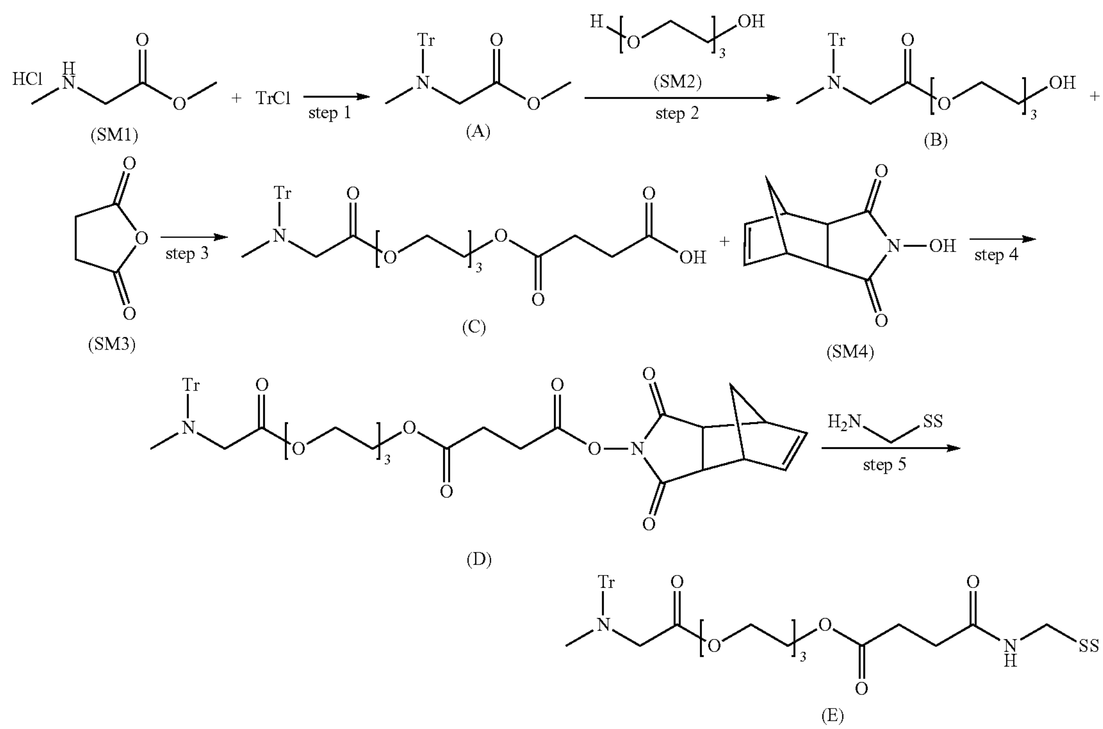

(SM1) (A) (SM2) (B) (SM3) (C) (SM4) (D) (E)

Step 1 Synthesis of Compound (A)

To a solution of compound (SM1) (35 g, 0.25 mol, 1 eq.) in DMF (350 mL) was charged DIPEA (0.75 mol, 3 eq.) and TrCl (0.5 mol, 2 eq.) successively. The reaction was stirred at 20-25° C. until TLC showed that compound (SM1) was consumed completely. To the reaction mixture was charged water (1400 mL, 40 vol.) and EtOAc (1400 mL, 40 vol.). The organic layer was separated and washed by 20% NaCl aqueous solution to remove DMF. The resulting organic layer was concentrated and purified through silica gel column to obtain 79 g white powder (compound (A)) in 91% yield. $^1$H-NMR ($CDCl_3$) δ: 7.56 (d, 6H), 7.30-7.28 (m, 6H), 7.20-7.18 (m, 6H), 3.71-3.68 (m, 3H). 2.95 (s, 2H), 2.04 (s, 3H).

Step 2 Synthesis of Compound (B)

To a solution of triglycol (10 eq.) in NMP (500 mL, 10 vol.) was charged 60% NaH (0.1 eq., dissolved in mineral oil) at 20-30° C., then stirred at 20-30° C. for 20 minutes. Then compound (A) (50 g, 1 eq.) was charged into the reaction mixture at 20-30° C. The reaction was stirred at 20-30° C. until most of compound (A) was consumed. After reaction, DCM/MTBE (3/7, 1000 mL, 20 vol.) and water (1000 mL, 20 vol.) were charged into the reaction mixture. The organic layers were separated and washed by brine. The resulting organic layer was concentrated to obtain a crude compound (B). The crude compound (B) was purified through silica gel column to obtain 47 g product in 70% yield. $^1$H-NMR ($CDCl_3$) δ: 7.56 (d, 6H), 7.30-7.28 (m, 6H), 7.20-7.18 (m, 6H), 4.36-4.34 (m, 2H), 3.75-3.60 (m, 8H), 3.60-3.59 (m, 2H), 3.05 (s, 2H), 2.15 (s, 3H).

Step 3 Synthesis of Compound (C)

To a solution of compound (B) (47 g, 1 eq.) in THE (470 mL) was charged succinic anhydride eq.). The reaction was stirred at 55° C. for 2.0 hours until TLC showed compound (B) was consumed completely. After reaction, the pH of the reaction mixture was adjusted to about 8.5 with 10% $NaHCO_3$ aqueous solution. Then MTBE (940 mL, 20 vol.) was added into the mixture and the aqueous layer was separated. The pH of the resulting aqueous layer was adjusted to 3-5 with 20% citric acid solution, then extracted with DCM (940 mL, 20 Vol.) and washed with 10% $Na_2SO_4$ aqueous solution (470 mL, 10 vol.) to obtain an organic phase. After concentration, 56 g yellow oil was obtained in 98% yield, which was telescoped to next step without further purification, $^1$H-NMR, ($CDCl_3$) δ: 7.46 (d, 6H), 7.17-7.21 (m, 6H), 7.07-7.10 (m, 6H), 4.20-4.24 (m, 2H), 4.17-4.15 (m, 2H), 3.65-3.50 (m, 8H), 2.96 (s, 2H), 2.54-2.52 (m, 4H), 2.05 (s, 3H).

Step 4 Synthesis of Compound (D)

To a solution of compound (C) (56 g, 1 eq.) in DCM (560 mL) was charged N-hydroxy-5-norbornene-2,3-dicarboxylic acid imide (HONB, 1.02 eq.), DMAP (0.33 eq.), DIPEA (2.5 eq.) and then EDCI (1.1 eq.). The reaction was stirred at 20-30° C. until TLC showed that compound (C) was consumed completely. The mixture was washed with 10% citric acid solution and brine successively. The organic layer was concentrated to dryness for next step without further purification. 67 g foam solid was obtained in 93% yield. $^1$H-NMR ($CDCl_3$) δ: 7.46 (d, 6H), 7.17-7.21 (m, 6H), 7.07-7.10 (6H), 6.11 (d, 2H), 4.20-4.24 (m, 2H), 4.17-4.15 (m, 2H), 3.65-3.50 (m, 8H), 3.36 (s, 2H), 3.23 (s, 2H), 2.96 (s, 2H), 2.79 (t, 2H), 2.63 (t, 2H), 2.05 (s, 3H), 1.70 (d, 1H), (d, 1H).

Step 5 Synthesis of Compound (E)

The aminomethyl polystyrene resin (10 g, loading amount was 1 mmol/g) (purchased from Xi'an Lanxiao Technology Co., Ltd.) was suspended into NMP (200 mL) and was allowed to swell for 1-2 hours. The suspension of resin was filtered to remove the NMP and washed with DCM 0.00 mL)

and 5% DIPEA in IPA/DCM (200 mL, v/v=1:3) successively. Compound (D) (2.5 eq.) solution in NMP (10 vol.) was charged into the suspension of aminomethyl polystyrene resin (10 g) in NMP (100 mL). The reaction mixture was stirred at 40-45° C. for 24-48 hours. The suspension was filtered, then washed with 100 mL NMP and 100 mL DCM. The wet cake was transferred into a reactor, followed by addition of NEM (0.4 M) solution in NMP (60 mL) and $Bz_2O$ (0.4 M) solution in NNW (60 mL). The remained amino groups in the resin were capped by $Bz_2O$. After the completion of the capping reaction, the resin was filtered and washed with DCM (100 mL), After dryness, the sarcosinate modified aminomethyl resin was obtained, which was used for phosphorodiamidate morpholino oligomer synthesis.

Determination of the Loading Amount

Typical Procedure:

The loading of the resin (number of potentially available reactive sites) was determined by a spectrometric assay for the known weight of dried resin (25+3 mg) was transferred to a silanized 25 mL volumetric flask and about 5 mL of 2% (v/v) trifluoroacetic acid in dichloromethane was added. The contents were mixed by gentle swirling and then allowed to stand for 30 minutes. The volume was brought up to 25 mL with additional 2% (v/v) trifluoroacetic acid in dichloromethane and the contents thoroughly mixed. Using a positive displacement pipette, an aliquot of the trityl-containing solution (500 μL) was transferred to a 10 mL volumetric flask and the volume brought up to 10 mL with methanesulfonic acid. The trityl cation content in the final solution was measured by UV absorbance at 406 nm and the resin loading calculated in trityl groups per gram resin (μmol/g) using compound A as the reference standard. The assay was performed in twice and an average loading calculated, the results were shown in table 1.

TABLE 1

| The loading amount of compound E | | | | |
|---|---|---|---|---|
| — | Batch | Times | Weight | Average loading |
| Compound E | 1 | 2 | 7 g | 608 μmol/g |
| | 2 | 2 | 32 g | 619 μmol/g |

Example 2 Phosphorodiamidate Morpholino Oligomer Synthesis

Phosphorodiamidate morpholino oligomer synthesis was achieved by 25 cycles phosphorodiamidate morpholino subunits assembling from sarcosinate modified aminomethyl resin. Synthetic Route of phosphorodiamidate morpholino oligomer synthesis is as follows.

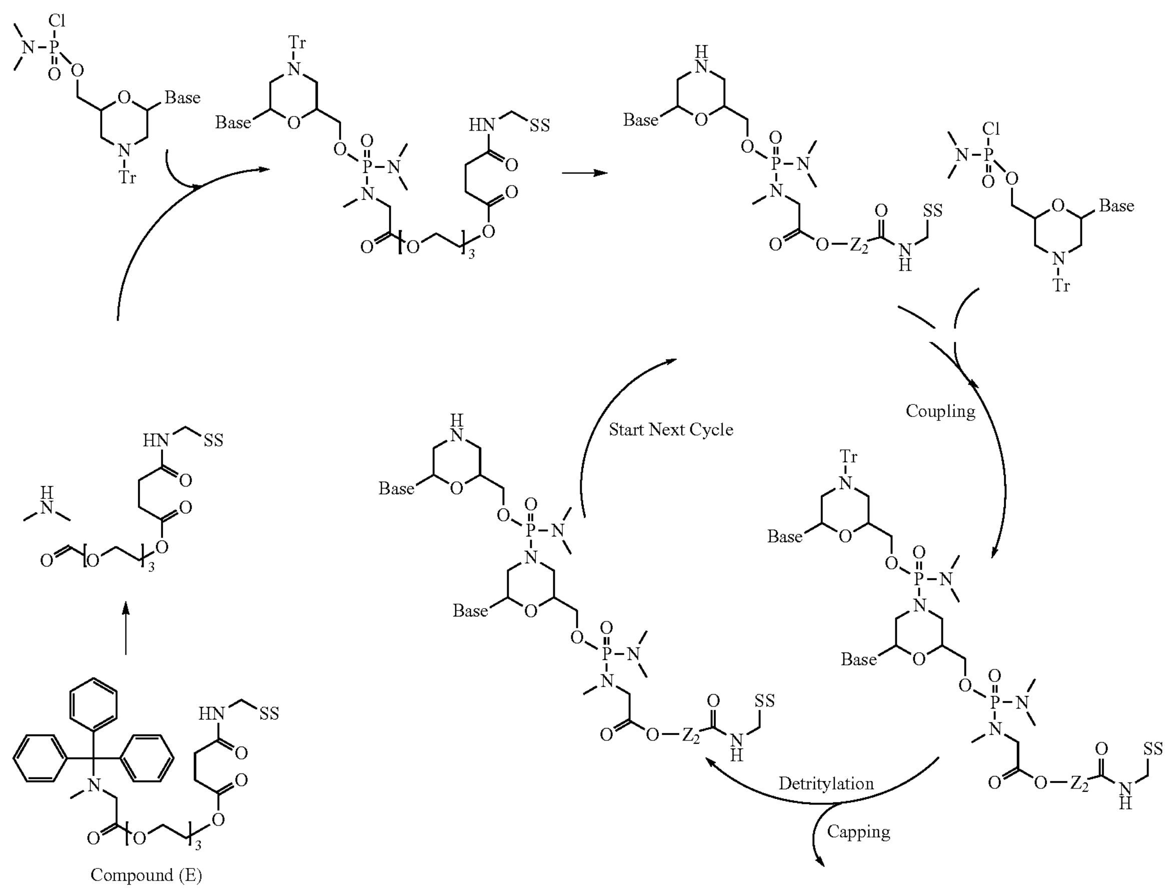

Compound (E)

-continued

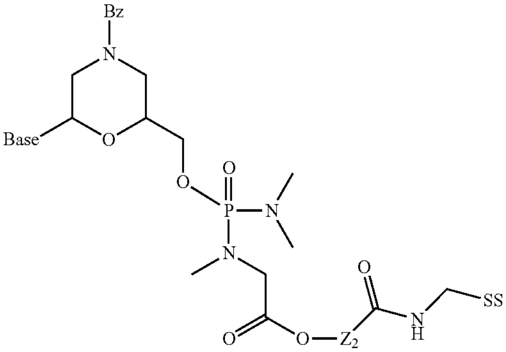

$Z_2$ =

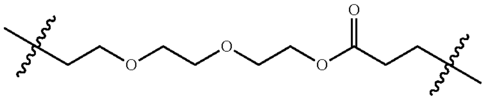

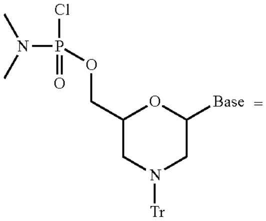

...

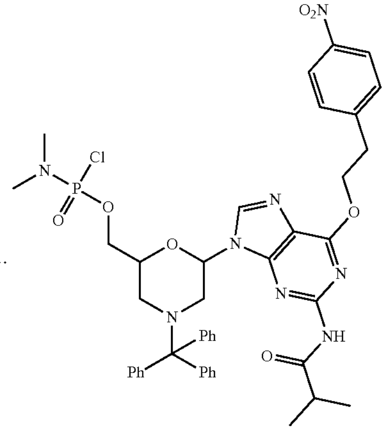

PMO NPEG monomer

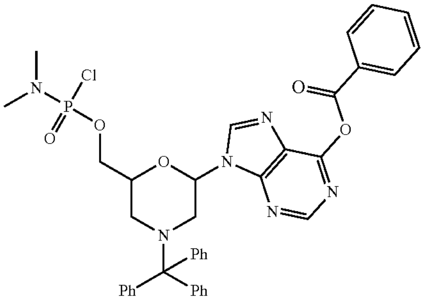

PMO PA monomer

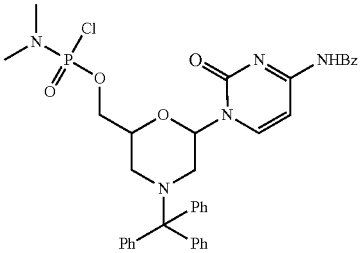

...

PMO PC monomer

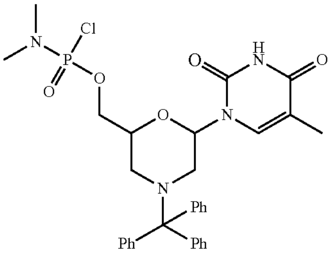

PMO T monomer

The synthesis of phosphorodiamidate morpholino oligomer was performed manually by solid phase synthesis from triglycol sarcosinate modified support using peptide synthetic apparatus for the detritylation, neutralization, coupling, capping and wash cycles. All the reactions were conducted in the glass jacket column, the column volume of which included 20 mL, 100 mL and 500 mL and 2 L.

Before assembling the monomers onto the solid support, all the solutions were prepared as follows.

Detritylation solution: 2% 4-cyanopyridinium trifluoroacetate (CYTFA) (w/v) in 20% trifluoroethanol/dichloromethane (1:4, v/v) with 1% ethanol.

Neutralization solution: 5% diisopropylethylamine in 25% isopropanol/dichloromethane.

Coupling solution: 0.36 M morpholino subunits solution in DMI and 0.8 M N-ethylmorpholine (NEM) in DMI. In the meantime, the morpholino subunits solution in DMI was treated with molecular sieve for over 12 hours to reduce the water content.

Capping Solution: 0.4 M NEM in NMP as Capping A; 0.4 M benzoic anhydride or acetic anhydride in NMP as Capping B.

TABLE 2

Reaction Solutions in Phosphorodiamidate Morpholino Oligomer Synthesis

| STEP | Reagent (s) | Reagent Composition |
|---|---|---|
| Wash | N-Methylpyrrolidinone (NMP) | 100% |
| | Dichloromethane(DCM) | 100% |
| Detritylation | 4-Cyanopyridine Trifuloroacetic acid (TFA) | 2% 4-cyanopyridinium trifluoroacetate in 2,2,2-trifluoroethanol/ |

TABLE 2-continued

Reaction Solutions in Phosphorodiamidate Morpholino Oligomer Synthesis

| STEP | Reagent (s) | Reagent Composition |
|---|---|---|
| | 2,2,2-Trifluoroethanol<br>DCM<br>EtOH | DCM ¼ with 1%<br>EtOH |
| Neutralization | Diisopropyl ethylamine<br>(DIPEA)<br>Isopropanol(IPA)<br>Dichloromethane(DCM) | 5% DIPEA in 1:3<br>isopropanol/DCM |
| Coupling | PMO monomers<br>N-Ethylmorpholine (NEM)<br>1,3-Dimethylimidazolidinone<br>(DMI) | 0.36M PMO<br>monomer in DMI,<br>0.8M NEM in DMI |
| Capping A | N-Ethylmorpholine (NEM)<br>N-Methylpyrrolidinone (NMP) | 0.4M NEM in NMP |
| Capping B | Benzoic Anhydride<br>N-Methylpyrrolidinone (NMP) | 0.4M Benzoic<br>anhydride in NMP |

To a jacket column reactor was charged sarcosinate modified aminomethylpolystyrene resin followed by 15 vol. 1-methyl-2-pyrrolidinone (NMP 15 mL/g resin), and the suspension was allowed to sit for 0.5-1 hour. Then NMP was evacuated and the resin was washed with DCM for five times before detritylation. To assemble each phosphorodiamidate morpholino oligomers subunit onto the support, four reactions would be conducted.

Firstly, to remove the trityl group on the support, 2% of 4-cyanopyridinium trifluoroacetate (CYTFA) (w/v) solution (2,2,2-trifluoroethanol/DCM ¼ with 1% EtOH) (15-25 vol.) was charged into the column reactor. The mixture was bubbled up with $N_2$ for 2-5 minutes and then evacuated to remove the solvent. This operation was repeated to 5-9 times until IPC showed that all trityl group was removed (IPC: the filtrate was sampled and diluted with methanesulfonic acid. The UV absorption at 411 nm was tested by UV spectrometer to check whether the trityl group was removed completely).

Secondly, after detritylation to the jacket column was charged 5% DIPEA in IPA/DCM (1/3) to neutralize the resin. Before coupling, the residual CYTFA need to be removed completely by multiple wash.

Thirdly, the coupling was conducted by charging the morpholino subunits solution and NEM solution in DMI into the reactor and the reaction was bubbled up with $N_2$ at 45° C. for 90 minutes. After assembling the morpholino subunits onto the support, the reaction mixture was evacuated and washed by DCM.

Lastly, the unreacted morpholino subunits on the support was capped to stop the elongation.

The four reactions were repeated as the following Table 3 until the target sequence was complete.

TABLE 3

Phosphorodiamidate Morpholino Oligomer Assembly Procedure

| Step | Volume (mL/g of starting resin 608 μmol/g) | Time(min) | Frequency |
|---|---|---|---|
| NMP | 15 V | 30-60 | 1 |
| DCM wash | 15 V | Flow through | 5 |
| Detritylation | 15-25 V | 2-5 | 5-9 |
| Neutralization | 15-25 V | 1-3 | 3 |
| DCM | 15-25 V | Flow through | 5 |
| Coupling | 10-25 V | 90 min at 45° C. | 1 |
| DCM wash | 15-25 V | Flow through | 2 |
| Neutralization | 15-25 V | 1-2 | 3 |
| DCM wash | 15-25 V | Flow through | 7 |

TABLE 3-continued

Phosphorodiamidate Morpholino Oligomer Assembly Procedure

| Step | Volume (mL/g of starting resin 608 μmol/g) | Time(min) | Frequency |
|---|---|---|---|
| Capping | CAP A: 5-10 V<br>CAP B: 5-10 V | 5-10 | 1 |
| DCM wash | 15-25 V | Flow through | 5 |

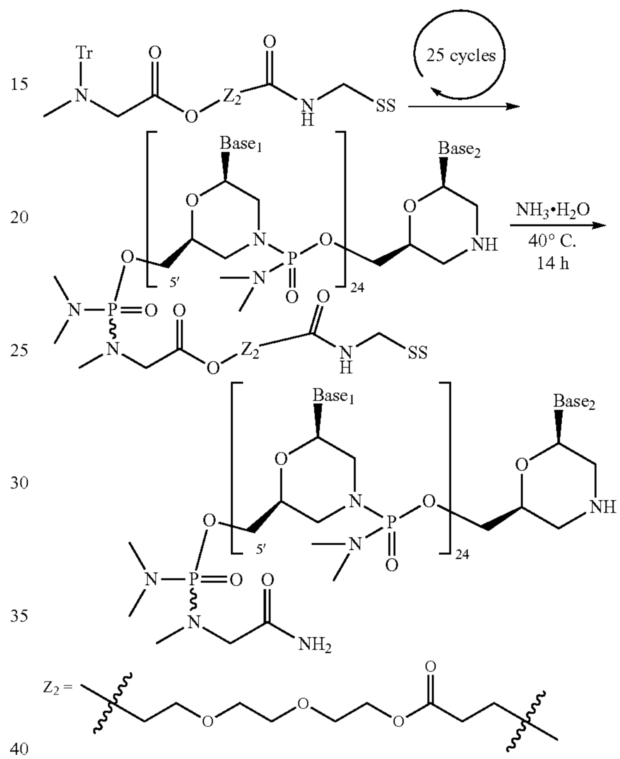

One phosphorodiamidate morpholino oligomer synthesis was conducted using 250 mg compound (E) with 608 μmol/g loading and 2.5 eq. phosphorodiamidate morpholino subunit (PMO-NPEG monomer, PMO-PA monomer, PMO-PC monomer, PMO-T monomer, the structures of which were shown in example 2) for each coupling reaction. After 25 cycles of reaction, 2.95 g wet base-protected phosphorodiamidate morpholino oligomer modified solid support was obtained. The base-protected phosphorodiamidate morpholino oligomer modified solid support was treated with 0.5 M DBU in NMP (20 mL) at 15° C. for 4 hours to remove 4-nitrophenethyl group and conc. ammonia hydroxide to cleave base-protected phosphorodiamidate morpholino oligomer and remove other protecting group successively. 28.8% of 4-nitrostyrene adduct impurities were found (determined by LC-MS), which significantly reduce the yield of phosphorodiamidate morpholino oligomer synthesis.

To address the 4-nitrostyrene adduct impurities issue, a three steps of cleavage and deprotection strategies were developed. The base-protected phosphorodiamidate morpholino oligomers was charged slowly (5 mL/min) into a DBU and thymine solution in NMP (the concentration of DBU was 0.8 M, and the concentration of thymine was 1.0 M). Those skilled in the art know that when the target phosphorodiamidate morpholino oligomers sequence contains thymine, then the concentration of thymine should be much larger than the concentration of thy mine in the target phosphorodiamidate morpholino oligomers sequence, e.g., the molar ratio of the thymine to the thymine in the target phosphorodiamidate morpholino oligomer sequence is greater than 10:1. After three steps of cleavage and deprotection, the 4-nitrostyrene adduct impurities were reduced significantly (below 5%, which was determined by LC-MS).

Three Steps of Cleavage and Deprotection

After solid phase assembly, a base-protected phosphorodiamidate morpholino oligomer modified solid support with 4-nitrophenethyl group on guanine was obtained. Then three steps of cleavage and deprotection were carried out as follows.

Step (1), the base-protected phosphorodiamidate morpholino oligomer crude product was cleaved first using conc. ammonia hydroxide (25%-28% ammonia hydroxide) to obtain an aqueous solution, which was lyophilized or concentrated to dryness to produce a base-protected phosphorodiamidate morpholino oligomer crude product.

Step (2), the crude product of step (1) was re-dissolved into NMP (the volume-mass ratio of NMP to the crude product was 10 mL/g) and charged into DBU/thymine (1.0 M/0.8 M) solution in NMP (10 Vol. relative to crude product) slowly (5 mL/min) to remove the 4-nitrophenethyl group while minimizing the 4-nitrostyrene adduct impurities.

Step (3), the oligonucleotides obtained after NPE deprotection was treated with conc. ammonia hydroxide (25%-28% ammonia hydroxide) again to remove remaining protecting groups such as isobutyryl to form targeted phosphorodiamidate morpholino oligomer A (PMO-A), the sequence was: 5'-GTT GCC TCC GGT TCT GAA GGT GTT C-3' (SEQ ID NO: 1).

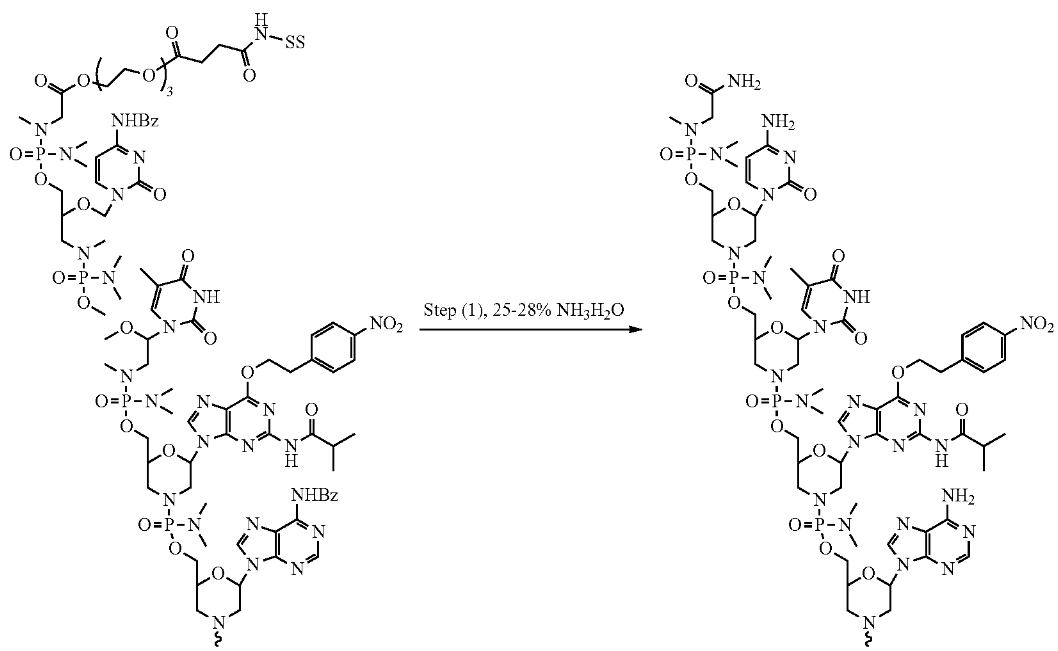

-continued

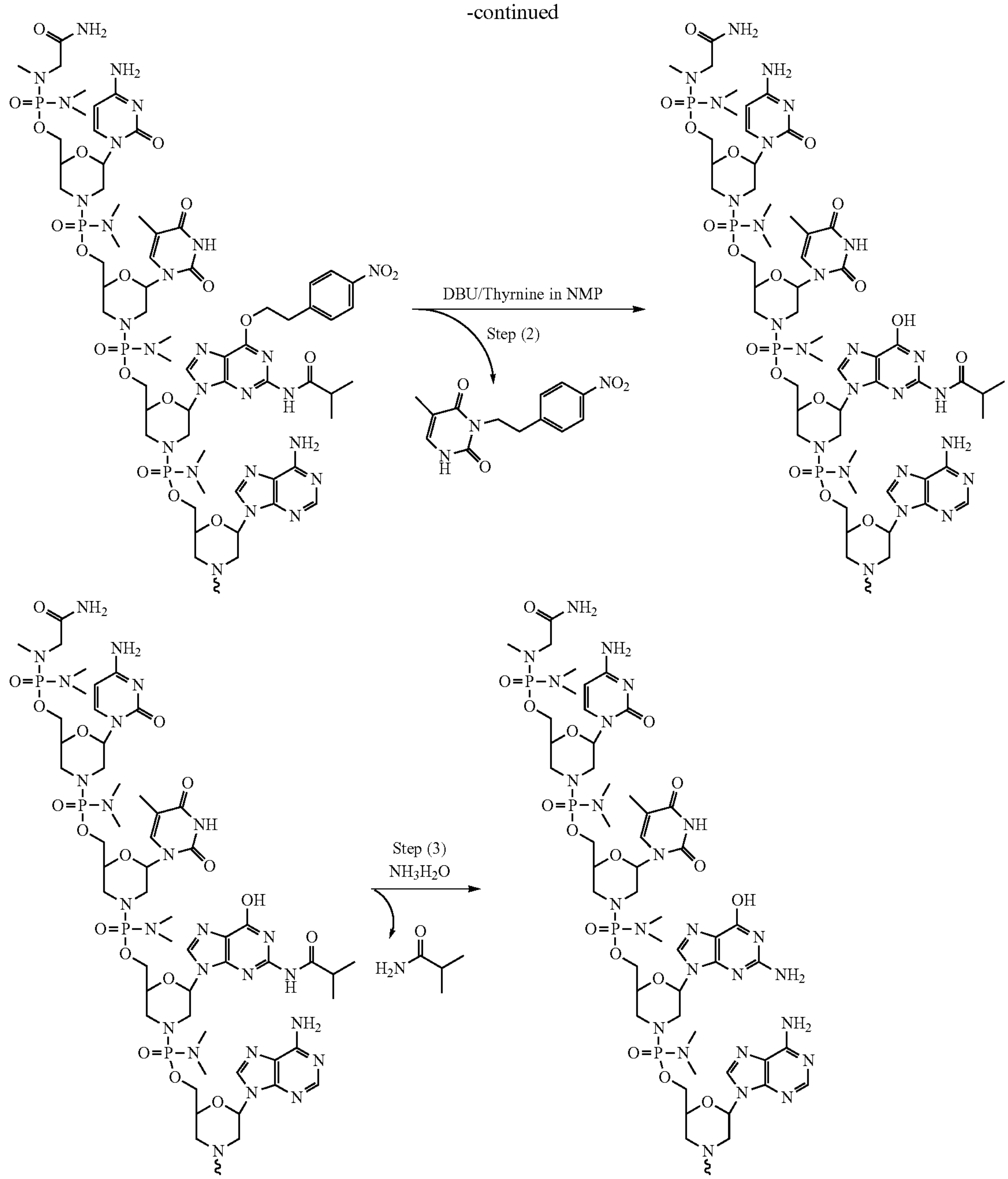

PMO-B, PMO-C, PMO-D and PMO-E were prepared by using the same method for preparing PMO-A.

The sequence of bases of PMO-B was 5'-CTC CAA CAT CAA GGA AGA TGG CAT TTC TAG-3' (SEQ ID NO: 2).

The sequence of bases of PMO-C was 5'-CTATATATAGTTATTCAACA-3' (SEQ ID NO: 3).

The sequence of bases of PMO-D was 5'-GGC CAAACC TCG GCT TAC CTG AAA T-3' (SEQ ID NO: 4).

The sequence of bases of PMO-E was 5'-CAG CAG CAG CAG CAG CAG-3' (SEQ ID NO: 5).

Several typical impurities were found during phosphorodiamidate morpholino oligomers synthesis, the results were shown in table 4.

TABLE 4

Typical impurities found in phosphorodiamidate morpholino oligomer synthesis

| — | LC-MS Purity | | | | | | |
|---|---|---|---|---|---|---|---|
| — | FLP Purity | N-A | N-C | N-G | N-T | OH | N + NPE |
| PMO-A | 5′-GTT GCC TCC GGT TCT GAA GGT GTT C-3′ (SEQ ID NO: 1) | | | | | | |
| Crude | 73.0% | 1.9% | 2.8% | 7.5% | 5.7% | 2.6% | 6.4% |
| After purification | 87.2% | 1.2% | 3.5% | 0.49% | 1.4% | 1.8% | 1.3% |
| PMO-B | 5′-CTC CAA CAT CAA GGAAGATGG CAT TTC TAG-3′ (SEQ ID NO: 2) | | | | | | |
| Crude | 67.33% | 5.96% | 4.28% | 6.29% | 5.11% | 6.01% | 5.02% |
| After AEX Purification | 85.74% | 0.79% | 3.53% | 0.74% | 4.15% | 0.75% | 4.3% |
| PMO-C | 5′-CTATATATAGTTATCCAACA-3′ (SEQ ID NO: 3) | | | | | | |
| Crude | 78.26% | 7.78% | 3.25% | 1.27% | 5.17% | 4.27% | N/A |
| After Purification | 86.79% | 5.38% | 3.92% | N/A | 1.88% | 2.03% | N/A |
| PMO-D | 5′-GGC CAA ACC TCG GCT TAC CTG AAA T-3′ (SEQ ID NO: 4) | | | | | | |
| Crude | 81.93% | 1.99% | 2.69% | 2.17% | 1.18% | 5.24% | 4.81% |
| Purification | 90.15% | 1.60% | 2.48% | 1.28% | 1.12% | 0.71% | 2.66% |
| PMO-E | 5′-CAG CAG CAG CAG CAG CAG-3′ (SEQ ID NO: 5) | | | | | | |
| Crude | 80.65% | 1.96% | 2.58% | 2.05% | N/A | 6.42% | 1.08% |
| Purification | 88.9% | 1.68% | 1.88% | 2.71% | N/A | 1.52% | 1.2% |

FLP purity represents for LC-MS purity of the full length product.

N-A, N-C, N-G, N-T represent for four impurities of N−1.

OH represents for impurities of phosphoryl dimethylamine hydrolysis.

N+NPE represents for 4-nitrostyrene adduct impurities.

LC-MS: Waters H-Class UPLC with Xevo G2-XS-TOF detector.

Crude product refers to the PMOs obtained after the three steps cleavage and deprotection without purification.

Purification product refers to the PMOs obtained after the three steps cleavage and deprotection and then purified using ion exchange chromatography.

It is to be understood that the foregoing description of two preferred, embodiments is intended to be purely illustrative of the principles of the invention, rather than exhaustive thereof, and that changes and variations will be apparent to those skilled in the art, and that the present invention is not intended to be limited other than expressly set forth in the following claims.

The invention claimed is:

1. A process for preparing an oligonucleotide comprising:

(a) converting a compound of Formula X-1 into a compound of Formula X-2:

X-1

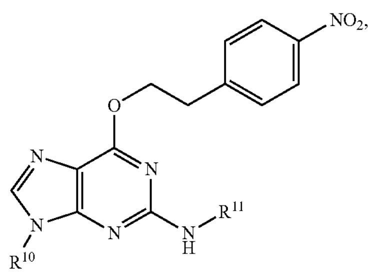

X-2

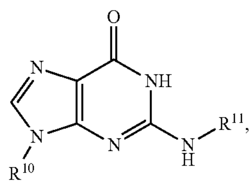

wherein:

$R^{10}$ is a residue of a phosphorodiamidate morpholino oligomer;

$R^{11}$ is an amine protecting group;

wherein the compound of Formula X-1 is not bound to a solid support; and (b) optionally removing protecting groups in the compound of Formula X-2 to obtain the oligonucleotide, wherein the converting comprises adding the compound of Formula X-1 in a solution, into a mixture comprising an alkaline reagent, and a scavenger capable of reacting with the compound of Formula X-3:

X-3

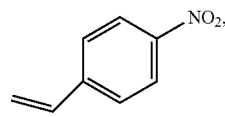

wherein the scavenger has a —SH or a 1,3-dicarbonyl moiety.

2. The process of claim 1, wherein the alkaline reagent is a basic organic amine having a pKa in water of about 9 or higher.

3. The process of claim 1, wherein the scavenger is a compound of X-4:

X-4

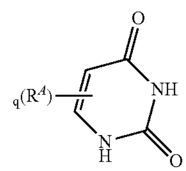

wherein:

q is 0, 1, or 2, and $R^A$ at each occurrence is independently an optionally substituted $C_{1-6}$ alkyl.

4. The process of claim 1, wherein the scavenger is thymine or a derivative thereof.

5. The process of claim 1, wherein $R^{11}$ is an amine protecting group that can be removed by treatment with $NH_3$.

6. A process for preparing an oligonucleotide comprising:

(a) converting a compound of Formula X-5 into a compound of Formula X-6:

X-5

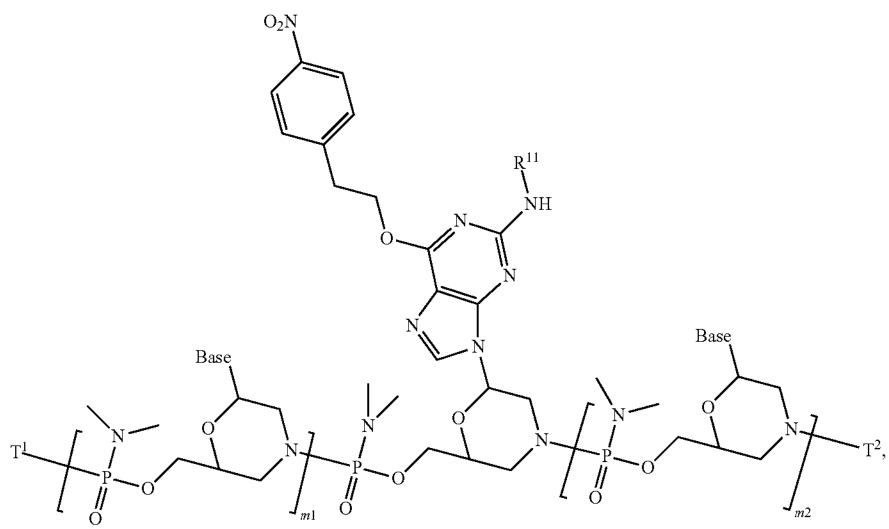

X-6

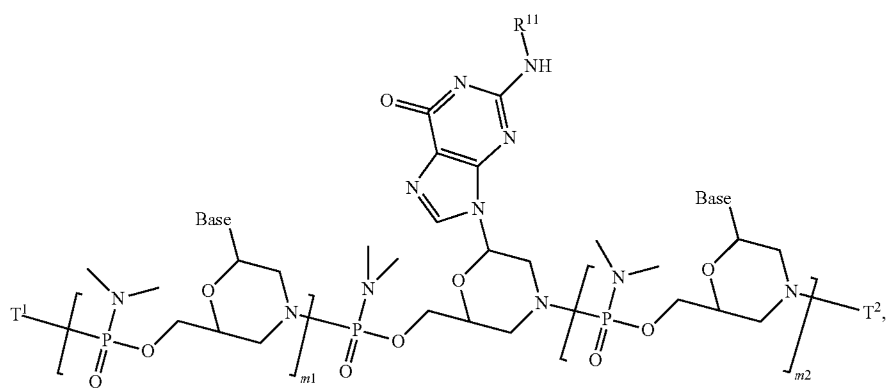

wherein:

m1 and m2 are independently an integer of 0-50;

$R^{11}$ is an amine protecting group;

Base at each occurrence is independently a base selected from G (guanine), C (cytosine), A (adenine), U (uracil), and T (thymine), modified analogs thereof, and protected derivatives thereof, provided that when the Base in Formula X-5 is a protected base, the corresponding Base in Formula X-6 can be the same protected base or a corresponding partially or fully deprotected base;

wherein:

$T^1$ is a suitable 5' terminal group; and $T^2$ is a suitable 3' terminal group; and (b) optionally partially or fully removing protecting groups in the compound of Formula X-6 to obtain the oligonucleotide.

7. The process of claim 6, wherein Base in Formula X-5 or X-6 at each occurrence is independently selected from the group consisting of

PC

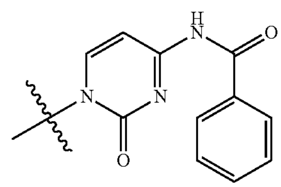

T

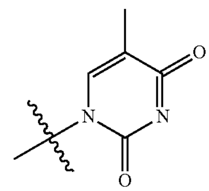

-continued

PA

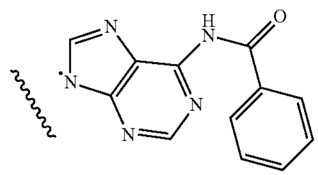

P5mC

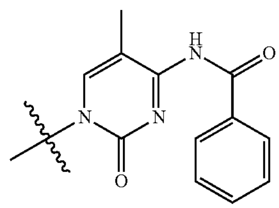

DPG

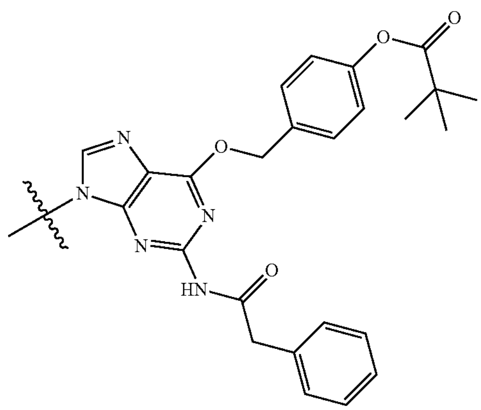

U

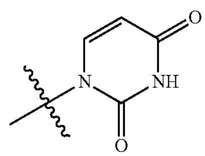

I

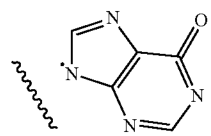

PG

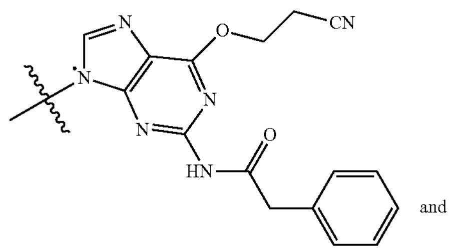

and

-continued

NPEG

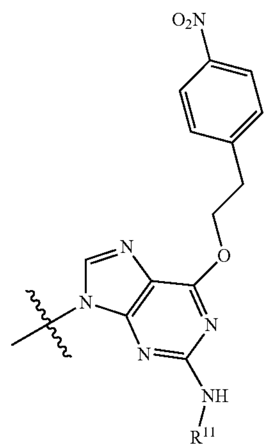

, wherein $R^{11}$ is an amine protecting group.

8. The process of claim 6, wherein one of m1 and m2 is 0, or neither of m1 or m2 is 0.

9. The process of claim 6, wherein the sum of m1 and m2 is between 5 and 50.

10. The process of claim 6, wherein $T^1$ is an optionally substituted alkyl amine or an optionally substituted heterocyclic ring.

11. The process of claim 6, wherein $T^2$ is hydrogen, trityl or an acyl group.

12. The process of claim 6, wherein the converting comprises adding the compound of Formula X-5 in a solution, into a mixture comprising an alkaline reagent and a scavenger capable of reacting with the compound of Formula X-3:

X-3

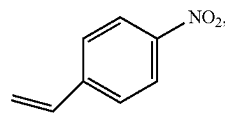

wherein the scavenger has a —SH or a 1,3-dicarbonyl moiety.

13. The process of claim 12, wherein the alkaline reagent is a basic organic amine having a pKa in water of about 9 or higher.

14. The process of claim 12, wherein the scavenger is a compound of X-4:

X-4

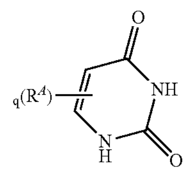

wherein:

q is 0, 1, or 2, and $R^A$ at each occurrence is independently an optionally substituted $C_{1-6}$ alkyl.

15. The process of claim 12, wherein the scavenger is thymine or a derivative thereof.

16. The process of claim 12, wherein $R^{11}$ is an amine protecting group that can be removed by treatment with $NH_3$.

17. The process of claim 6, further comprising treating the compound of Formula X-6 with $NH_3$ to partially or fully remove the protecting groups in Formula X-6.

18. The process of claim 6, wherein the compound of Formula X-5 is prepared by a process comprising cleaving a solid support from an oligonucleotide of Formula X-7:

X-7

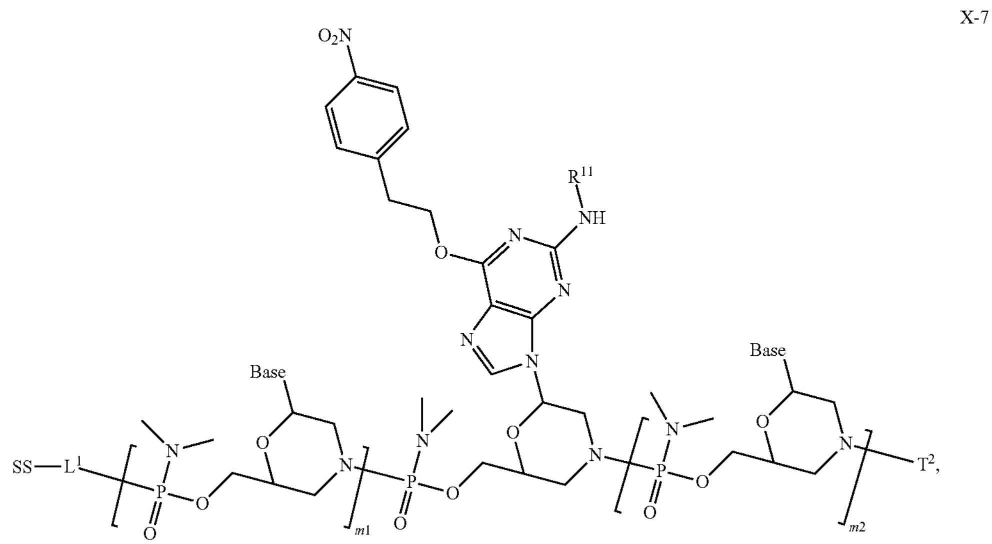

wherein

SS is a solid phase support, $L^1$ is a linker;

m1, m2, and $R^{11}$ in Formula X-7 are the same as the corresponding groups in Formula X-5, Base at each occurrence is independently a base selected from G (guanine), C (cytosine), A (adenine), U (uracil), and T (thymine), modified analogs thereof, and protected derivatives thereof, provided that when the Base in Formula X-7 is a protected base, the corresponding base in Formula X-5 can be the same protected base or a corresponding partially or fully deprotected base; and $T^2$ is a suitable 3' terminal group.

* * * * *

SEQUENCE LISTING

```
Sequence total quantity: 5
SEQ ID NO: 1           moltype = DNA  length = 25
FEATURE                Location/Qualifiers
misc_feature           1..25
                       note = PMO-A
source                 1..25
                       mol_type = other DNA
                       organism = synthetic construct
SEQUENCE: 1
gttgcctccg gttctgaagg tgttc                                      25

SEQ ID NO: 2           moltype = DNA  length = 30
FEATURE                Location/Qualifiers
misc_feature           1..30
                       note = PMO-B
source                 1..30
                       mol_type = other DNA
                       organism = synthetic construct
SEQUENCE: 2
ctccaacatc aaggaagatg gcatttctag                                 30
```

-continued

```
SEQ ID NO: 3            moltype = DNA  length = 20
FEATURE                 Location/Qualifiers
misc_feature            1..20
                        note = PMO-C
source                  1..20
                        mol_type = other DNA
                        organism = synthetic construct
SEQUENCE: 3
ctatatatag ttattcaaca                                        20

SEQ ID NO: 4            moltype = DNA  length = 25
FEATURE                 Location/Qualifiers
misc_feature            1..25
                        note = PMO-D
source                  1..25
                        mol_type = other DNA
                        organism = synthetic construct
SEQUENCE: 4
ggccaaacct cggcttacct gaaat                                  25

SEQ ID NO: 5            moltype = DNA  length = 18
FEATURE                 Location/Qualifiers
misc_feature            1..18
                        note = PMO-E
source                  1..18
                        mol_type = other DNA
                        organism = synthetic construct
SEQUENCE: 5
cagcagcagc agcagcag                                          18
```